United States Patent [19]

Brown

[11] Patent Number: 4,659,361
[45] Date of Patent: Apr. 21, 1987

[54] HERBICIDAL IODOPYRIMIDINES

[75] Inventor: Hugh M. Brown, West Grove, Pa.

[73] Assignee: E. I. Du Pont de Nemours and Company, Wilmington, Del.

[21] Appl. No.: 721,602

[22] Filed: Apr. 12, 1985

Related U.S. Application Data

[63] Continuation-in-part of Ser. No. 619,276, Jun. 11, 1984, abandoned.

[51] Int. Cl.$^4$ .................. A01N 47/36; C07D 239/47
[52] U.S. Cl. ........................................ 71/90; 71/91; 71/92; 544/320; 544/321; 544/3
[58] Field of Search ............... 71/92, 90, 91; 544/321, 544/332, 331, 320, 34

[56] References Cited

U.S. PATENT DOCUMENTS 4,600,428  7/1980  Szczepanski ........................ 71/76

FOREIGN PATENT DOCUMENTS 107979  10/1983  European Pat. Off. ............ 544/321

Primary Examiner—Robert Gerstl

[57] ABSTRACT

Specific iodopyrimidine compounds such as 2-[[(4-iodo-6-methoxypyrimidin-2-yl)aminocarbonyl]-aminosulfonyl]benzoic acid, methyl ester and N'-[(4-iodo-6-methoxypyrimidin-2-yl)aminocarbonyl]-N,N-dimethyl-1,2-benzenedisulfonamide are active preemergent and postemergent herbicides and plant growth regulants.

32 Claims, No Drawings

HERBICIDAL IODOPYRIMIDINES

RELATED APPLICATION

This application is a continuation-in-part of my co-pending application U.S. Ser. No. 619,276 filed June 11, 1984 now abandoned.

BACKGROUND OF THE INVENTION

The present invention relates to specific iodopyrimidine compounds which are useful as general or selective preemergent or postemergent herbicides or as plant growth regulants.

U.S. Pat. No. 4,394,506, issued July 19, 1983 to Levitt discloses herbicidal N-(heterocyclicaminocarbonyl)arylsulfonamides of the formula

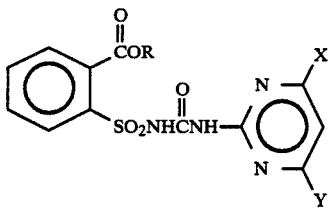

wherein, among other substituents, X may be $OCH_3$ or $OC_2H_5$ and Y may be F, Cl, or Br.

SUMMARY OF THE INVENTION

This invention relates to novel compounds of Formula I, argiculturally suitable compositions containing them, and their method-of-use as general or selective preemergent or postemergent herbicides or as plant growth regulants.

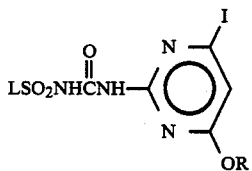 I wherein
R is $CH_3$ or $CH_2CH_3$;

L is 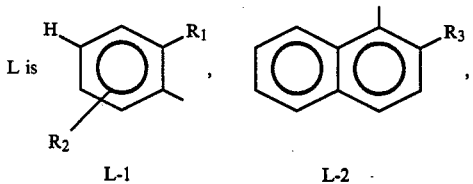

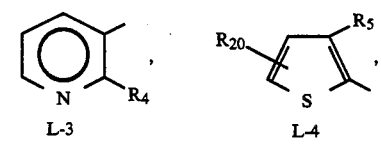

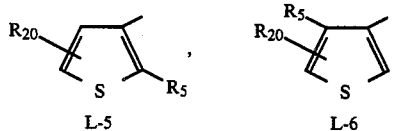

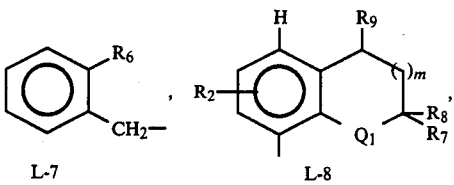

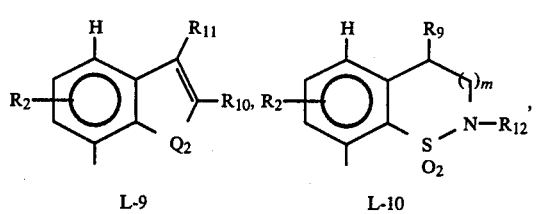

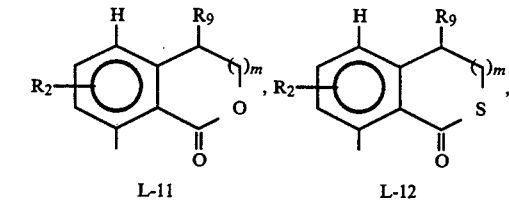

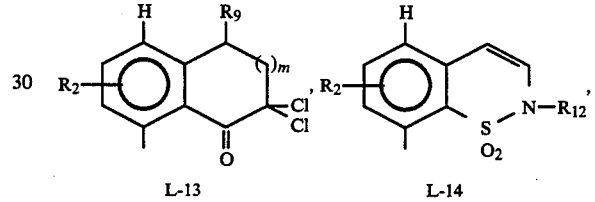

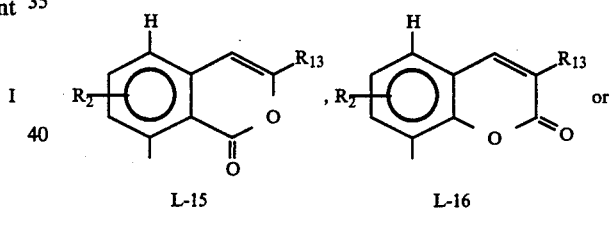

$R_1$ is $C_1-C_4$ alkyl, $C_1-C_4$ alkoxy, $OCH_2CH_2OCH_3$, F, Cl, Br, $NO_2$, $CF_3$, $CO_2R_{15}$, $SO_2NR_{16}R_{17}$, $C(O)R_{21}$, $CR_{21}(OR_{22})_2$, $SO_2N(OCH_3)CH_3$, $OSO_2R_{18}$, $S(O)_nR_{19}$, $WCF_3$, $WCHF_2$, $C_3-C_4$ alkenyloxy, $C_3-C_4$ alkynyloxy, $C_1-C_2$ alkyl substituted with $OCH_3$ or $OCH_2CH_3$, $C_6H_5$,

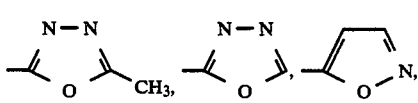

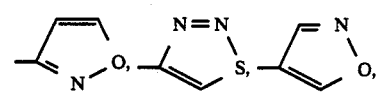

-continued

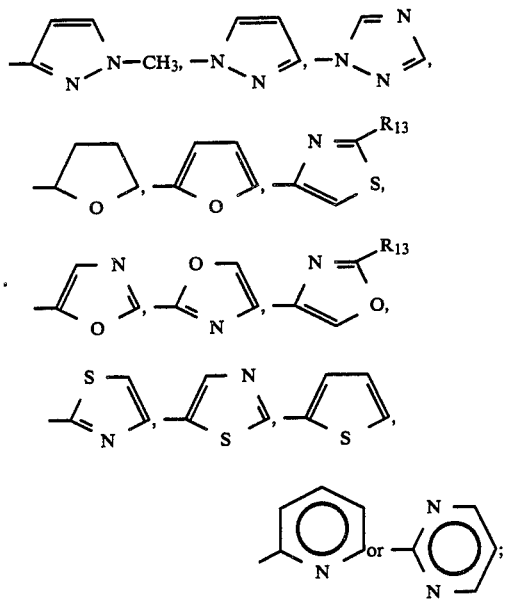

$R_2$ is H, F, Cl, Br, $C_1$-$C_4$ alkyl, $C_1$-$C_4$ alkoxy, $C_3$-$C_4$ alkenyloxy, $C_3$-$C_4$ alkynyloxy, $C_1$-$C_4$ haloalkoxy, $C_1$-$C_4$ haloalkyl, $S(O)_p C_1$-$C_4$ alkyl, $S(O)_p C_3$-$C_4$ alkenyl, $S(O)_p C_3$-$C_4$ alkynyl or $C_1$-$C_2$ alkyl substituted with $OCH_3$ or $SCH_3$;

$R_3$ is H, $CH_3$, $OCH_3$, F, Cl, Br, $SO_2N(CH_3)_2$, $OSO_2CH_3$ or $S(O)_n CH_3$;

$R_4$ is $CH_3$, $CH_2CH_3$, $OCH_3$, $OCH_2CH_3$, F, Cl, Br, $SO_2NR_{16}R_{17}$, $SO_2N(OCH_3)CH_3$, $S(O)_n R_{19}$, $C_3$-$C_4$ alkenyloxy or $C_3$-$C_4$ alkynyloxy;

$R_5$ is $C_1$-$C_3$ alkyl, F, Cl, Br, $NO_2$, $CO_2R_{15}$, $SO_2NR_{16}R_{17}$, $SO_2N(OCH_3)CH_3$ or $S(O)_n R_{19}$;

$R_6$ is Cl, $NO_2$, $CO_2CH_3$, $CO_2CH_2CH_3$, $SO_2N(CH_3)_2$, $OSO_2CH_3$, $SO_2CH_3$, $SO_2CH_2CH_3$, $OCH_3$ or $OCH_2CH_3$;

$R_7$ is H, $CH_3$ or $CH_2CH_3$;
$R_8$ is H, $CH_3$ or $CH_2CH_3$;
$R_9$ is H or $CH_3$;
$R_{10}$ is H or $CH_3$;
$R_{11}$ is H or $CH_3$;
$R_{12}$ is H, $C_1$-$C_4$ alkyl, $C_3$-$C_4$ alkenyl, $C_3$-$C_4$ alkynyl, benzyl, $C_1$-$C_4$ alkylcarbonyl, $C_1$-$C_4$ alkoxycarbonyl, $CH_2CN$, $CH_2C(O)CH_3$, $CH_2CO_2(C_1$-$C_2$alkyl), $C_1$-$C_4$ alkyl substituted with 0-3F, 0-1Cl, OH, $OCH_3$ or $OC_2H_5$ or $C_3$-$C_4$ alkenyl substituted with 1-3F or 1-3Cl;
$R_{13}$ is H or $CH_3$;
$R_{14}$ is $CH_3$ or $C_2H_5$;
$R_{15}$ is $C_1$-$C_4$ alkyl, $CH_2CH_2OCH_3$, $CH_2CH_2Cl$ or $CH_2CH=CH_2$;
$R_{16}$ is H, $C_1$-$C_3$ alkyl;
$R_{17}$ is $C_1$-$C_3$ alkyl;
$R_{18}$ is $C_1$-$C_3$ alkyl or $N(CH_3)_2$;
$R_{19}$ is $C_1$-$C_3$ alkyl or $CH_2CH=CH_2$;
$R_{20}$ is H, Cl or $CH_3$;
$R_{21}$ is H, $C_1$-$C_4$ alkyl, $C_3$-$C_4$ alkenyl, $C_3$-$C_4$ alkynyl or $C_3$-$C_6$ cycloalkyl;
$R_{22}$ is $C_1$-$C_2$ alkyl;
m is 0 or 1;
n is 0 or 2;
p is 0, 1 or 2;
$Q_1$ is O, S or $SO_2$;
$Q_2$ is O or S; and
W is O, S or $SO_2$;
provided that
(1) the total number of carbon atoms of $R_{16}$ and $R_{17}$ is less than or equal to four; and
(2) when m is 1, then $R_9$ is H; and their agriculturally suitable salts.

Preferred for reasons of their higher herbicidal activity, greater plant growth regulant activity or more favorable ease of synthesis are:
(1) Compunds of Formula I where R is $CH_3$.
(2) Compounds of Preferred 1 where L is L-1, L-2, L-3, L-5, L-8, L-10, L-11, L-16 or L-17.
(3) Compounds of Preferred 2 where
L is L-1;
$R_1$ is $OCH_3$, $OC_2H_5$, Cl, $NO_2$, $CF_3$, $CO_2CH_3$, $CO_2C_2H_5$, $SO_2N(CH_3)_2$, $SO_2N(OCH_3)CH_3$, $OSO_2R_{18}$, $S(O)_n R_{19}$, $OCF_2H$, $SCF_2H$, $C(O)CH_3$, $C(O)C_2H_5$, $OCH_2CH=CH_2$, $OCH_2C\equiv CH$,

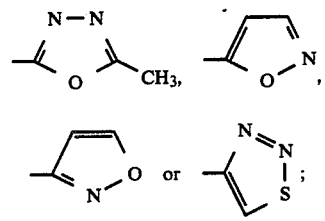

$R_2$ is H, F, Cl, Br, $CH_3$, $C_2H_5$, $S(O)_p C_1$-$C_2$ alkyl, $S(O)_p CH_2CH=CH_2$, $S(O)_p CH_2C\equiv CH$, $C_1$-$C_3$ alkoxy, $OCH_2CH=CH_2$, $OCH_2C\equiv CH$, $C_1$-$C_2$ haloalkoxy, $C_1$-$C_2$ haloalkyl, $CH_2OCH_3$ or $CH_2SCH_3$;
$R_{18}$ is $C_1$-$C_3$ alkyl;
$R_{19}$ is $CH_3$ or $C_2H_5$; and
n is 2.
(4) Compounds of Preferred 3 where
L is

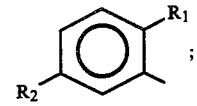

and
$R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.
(5) Compounds of Preferred 2 where
L is L-2; and
$R_3$ is Cl, $CH_3$, $OCH_3$, $SCH_3$ or Br.
(6) Compounds of Preferred 2 where
L is L-3; and
$R_4$ is Cl, $SO_2CH_3$ or $SO_2N(CH_3)_2$.
(7) Compounds of Preferred 2 where
$R_{20}$ is H;
L is L-5; and
$R_5$ is $CO_2CH_3$ or $CO_2C_2H_5$.
(8) Compounds of Preferred 2 where L is L-8.
(9) Compounds of Preferred 2 where
$R_9$ is H;
$R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.
L is L-10; and $R_{12}$ is H, $C_1$-$C_4$ alkyl, $C_1$-$C_4$ alkylcarbonyl, $CH_2F$ or $C_2$-$C_3$ alkyl substituted with 1F or 1Cl.

(10) Compounds of Preferred 2 where
  L is L-11;
  $R_9$ is H; and
  $R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.

(11) Compounds of Preferred 2 where
  L is L-16;
  $R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.

(12) Compounds of Preferred 2 where
  L is L-17;
  $R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.

Specifically preferred for reasons of their highest herbicidal activity, greatest growth regulant activity and/or most favorable ease of synthesis are:
  2-[[(4-iodo-6-methoxypyrimidin-2-yl)aminocarbonyl]aminosulfonyl]benzoic acid, methyl ester, m.p. 194°–196° C.(d);
  N'-[(4-iodo-6-methoxypyrimidin-2-yl)aminocarbonyl]-N,N-dimethyl-1,2-benzenedisulfonamide, m.p. 231°–232.5° C.; and
  2-[[(4-iodo-6-methoxypyrimidin-2-yl)aminocarbonyl]aminosulfonyl]-4-methylbenzoic acid, methyl ester, m.p. 185°–186° C.

DETAILED DESCRIPTION OF THE INVENTION

Synthesis

The compounds of Formula I can be prepared by one or more of the following methods described below in Equations 1, 4, 5 and 6.

As shown in Equation 1 below, compounds of Formula I can be prepared by reacting an appropriately substituted sulfonyl isocyanate of Formula II with an aminoheterocycle of Formula III where L and R are as previously defined.

Equation 1

$$LSO_2NCO + H_2N\text{-}Ar \longrightarrow LSO_2NHCNH\text{-}Ar$$

(where Ar is the pyrimidine bearing I and OR)

II     III

I

The reaction is best carried out in inert aprotic organic solvents such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent to a stirred solution of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane and heptane or by chromatography on silica gel.

Sulfonylisocyanates of Formula II are known in the art and are prepared from the corresponding sulfonamides (IV) by one of the following two general methods.

Equation 2

$$LSO_2NH_2 \xrightarrow[COCl_2, \text{ cat}]{CH_3(CH_2)_3NCO} LSO_2NCO$$

IV                                           II

The sulfonamide IV and an alkyl isocyanate (e.g., n-butyl isocyanate) in xylene or other solvent boiling above 135° C. are mixed in the presence or absence of a catalytic amount of 1,4-diaza[2.2.2]bicyclooctane (DABCO) and heated to 135°–140° C. After 5–60 minutes phosgene is slowly added to the heated mixture at such a rate that the temperature remains between 133° and 135° C. When the consumption of phosgene has ceased, the mixture is cooled and filtered to remove insoluble material. Finally, the solvent, alkyl isocyanate, and excess phosgene are evaporated, leaving the sulfonyl isocyanate (II).

If desired, the alkyl isocyanate-sulfonamide adduct can be made and isolated before reaction with the phosgene. In this case the sulfonamide (IV), alkyl isocyanate, and anhydrous base (e.g., $K_2CO_3$) in a polar, aprotic solvent (e.g., acetone, butanone, or acetonitrile) are mixed and heated under reflux for 1 to 6 hours. The reaction mixture is then diluted with water, and the pH is adjusted to about 3 with acid (e.g., HCl, $H_2SO_4$). The adduct is filtered out and dried, and then reacted with phosgene as described above. This procedure modification is especially useful when sulfonamide (IV) is high melting and has low solubility in the phosgenation solvent.

Sulfonyl isocyanates (II) can also be prepared by the following method.

Equation 3

(a) $LSO_2NH_2 \xrightarrow{SOCl_2} LSO_2NSO$ (IV)                        (V)

(b) (V) $\xrightarrow[\text{pyridine cat.}]{COCl_2,} LSO_2NCO$ (II)

The sulfonamide (IV) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (V) (Equation 3a).

The thionyl chloride is evaporated and the residue is treated with an inert solvent (e.g., toluene) containing at least one equivalent (typically 2–3 equivalents) of phosgene. A catalytic amount of pyridine (typically 0.1 equivalent) is added, and the mixture is heated to about 60°–140° C., with 80°–100° preferred. Conversion to the isocyanate (II) is usually substantially complete within 15 minutes to 3 hours (Equation 3b). The mixture is then cooled and filtered, and the solvent is evaporated, leaving the sulfonyl isocyanate (II).

Many of the compounds of Formula I can be prepared by the procedure shown in Equation 4.

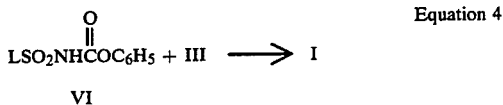

The reaction shown in Equation 4 is carried out by contacting phenylcarbamates of Formula VI with aminoheterocycles of Formula III in an inert organic solvent such as dioxane or tetrahydrofuran at temperatures of about 20°–100° C. for a period of about one-half to twenty-four hours. The product can be isolated by evaporation of the reaction solvent and purified by methods previously described.

Phenyl carbamates of Formula VI can be prepared by the methods described, or modifications thereof known to those skilled in the art, in European Patent Application No. 81810282.4 (Publ. No. 44,808), published Jan. 27, 1982; or South African Patent Application No. 825042.

Alternatively, many of the compounds of Formula I can be prepared by the method described in Equation 5.

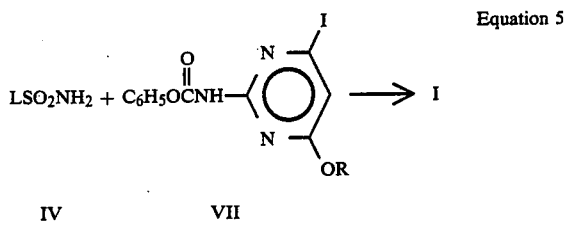

The reaction of Equation 5 can be carried out by contacting equimolar amounts of a sulfonamide of Formula IV with a heterocyclic phenylcarbamate of Formula VII in the presence of a base such as 1,8-diazabicyclo[5.4.0]undec-7-ene (DBU), by methods analagous to those described in South African Patent Application No. 830441. The phenyl carbamates of Formula VII can be prepared by methods, or modifications thereof known to those skilled in the art, described in South African Patent Application No. 825671 and South African Patent Application No. 825045.

Rarely, a sulfonamide of Formula IV may not be of sufficient stability to be useful as a starting material in any of the above procedures. In these cases, as well as others, the sulfonyl isocyanate of Formula II can be prepared as an unisolated intermediate by treating the corresponding sulfonyl chloride (VIII) with isocyanate anion in the presence of the heterocyclic amine of Formula III as shown in Equation 6.

The reaction is best carried out by adding over one to six hours a solution of at least one equivalent of a tetraalkylammonium isocyanate, such as tetra-n-butylammonium isocyanate, in a suitable aprotic organic solvent, such as dichloromethane or tetrahydrofuran, to a well-stirred mixture of one equivalent of sulfonyl chloride of Formula VIII and at least one equivalent of heterocyclic amine of Formula III in a similar suitable organic solvent at 20°–40° C. The reaction mixture is then diluted with dichloromethane, washed with 1N sulfuric acid, and dried over sodium sulfate. Rotary evaporation of the solvent leaves the product of Formula I in crude form. This may be purified as has already been described for Equation 1.

Certain sulfonyl chlorides are best prepared by chlorosulfonation of a substituted benzene, naphthalene, or thiophene in tetrachloromethane according to the teachings of H. T. Clarke et al., *Org. Synth. Coll.*, Vol. 1, 2nd Ed. 1941, p. 85. Other sulfonyl chlorides can be made by diazotization of the appropriate amine with sodium nitrite in hydrochloric acid, followed by reaction of the diazonium salt with sulfur dioxide and cuprous or cupric chloride in acetic acid according to the teachings of H. L. Yale and F. Sowinski, *J. Org. Chem.*, 25, 1824 (1960) and of H. Meerwein et al., *Chem. Ber.*, 90, 841 (1957).

Reference to the following patents is suggested for further details regarding the preparation of the sulfonamides (IV) and sulfonyl isocyanates (II): U.S. Pat. No. 4,169,719; U.S. Pat. No. 4,127,405; U.S. Pat. No. 4,394,506; and E.P.-A-No. 79,683.

Iodopyrimidines of Formula III can be prepared by the procedure shown in Equation 7.

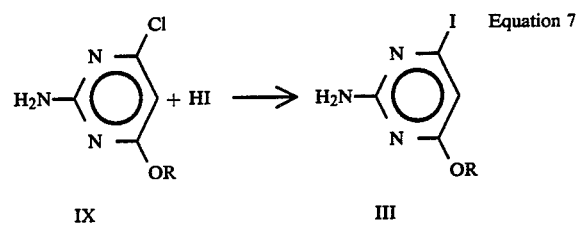

Treatment of a 2-amino-4-chloro-6-alkoxypyrimidines of Formula IX with 57% aqueous hydroiodic acid according to procedures found in *J. Chem. Soc. C*, 1204 (1967) gives the iodopyrimidines of Formula III. The chloropyrimidines of Formula IX are known in the art.

The following examples further illustrate the synthesis of this invention.

EXAMPLE 1

2-Amino-4-iodo-6-methoxypyrimidine 18.0 g of 2-amino-4-chloro-6-methoxypyrimidine was added to 65 mL of 57% aqueous hydroiodic acid with ice bath cooling. The resulting thick mixture was kept at ambient temperature for 65 hours, diluted with water and neutralized with potassium carbonate. The solid was collected and recrystallized from aqueous ethanol to give 5.0 g of white crystals, m.p. 141.5°–144° C.

NMR(CDCl$_3$): 3.82 (s, 3H, OCH$_3$); 5.3 (br s, 2H, NH$_2$); and 6.54 (s, 1H, pyr C5-H).

EXAMPLE 2

2-[[(4-iodo-6-methoxypyrimidin-2-yl)aminocarbonyl]aminosulfonyl]benzoic acid, methyl ester To a solution of 0.25 g of 2-amino-4-iodo-6-methoxypyrimidine in 5 mL of dry methylene chloride was added 0.30 g 2-carbomethoxybenzenesulfonyl isocyanate. The resulting solution was allowed to stand for 20 hours at ambient temperature. The solution was cooled in an ice bath and crystallization induced with scratching. The crystals were collected, washed with n-butylchloride and dried to afford 0.10 g of the title compound, m.p. b 194°-196° C. (dec).

IR (nujol) 1728 cm$^{-1}$ (ester) and 1705 cm$^{-1}$ (sulfonylurea).

NMR (CDCl$_3$): 3.94 (s, 3H, CO$_2$CH$_3$); 4.06 (s, 3H, OCH$_3$); 6.95 (s, 1H, pyr. C5-H); 7.4 (br s, 1H, NH); 7.75 (m, 3H, aromatics); 8.4 (m, 1H, aromatic); and 12.15 (br s, 1H, NH).

Using the procedures and examples shown above, the compounds in Tables 1-17 can be prepared.

General Structures for Tables

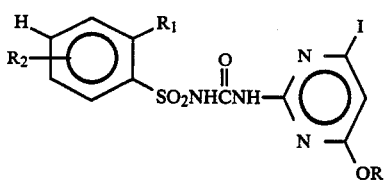

General Structure 1

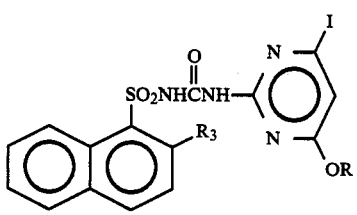

General Structure 2

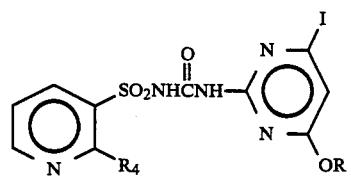

General Structure 3

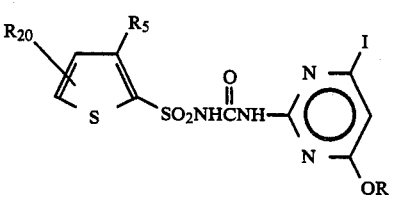

General Structure 4

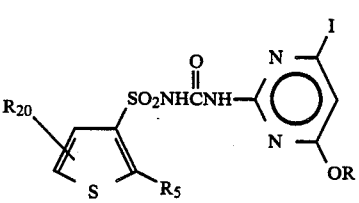

General Structure 5

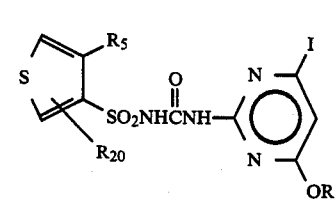

General Structure 6

-continued
General Structures for Tables

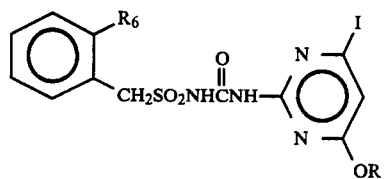

General Structure 7

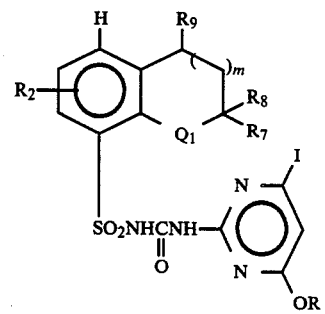

General Structure 8

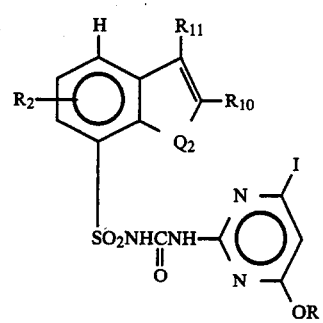

General Structure 9

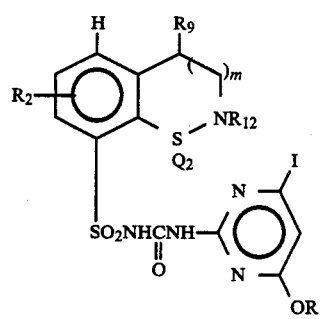

General Structure 10

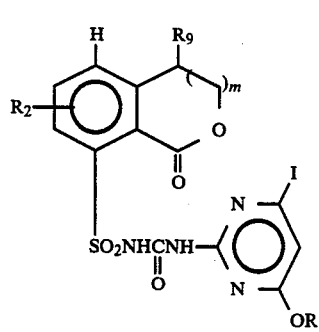

General Structure 11

-continued
General Structures for Tables

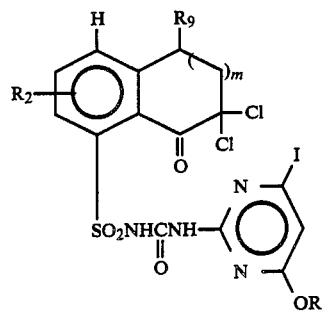
General Structure 12

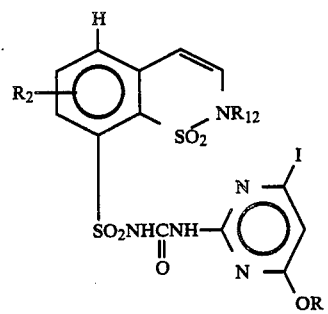
General Structure 13

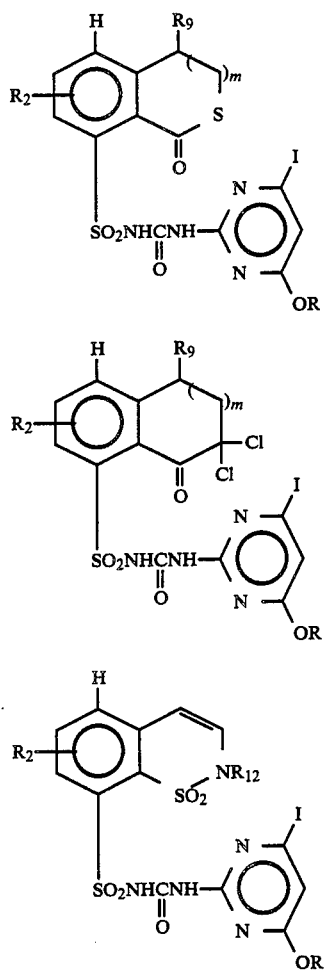
General Structure 14

-continued
General Structures for Tables

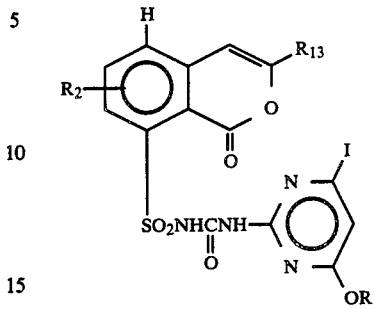
General Structure 15

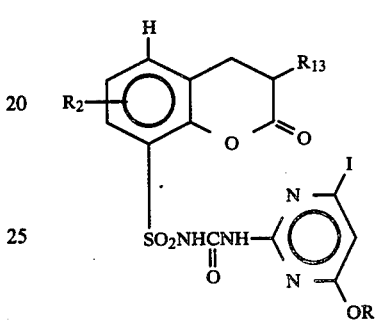
General Structure 16

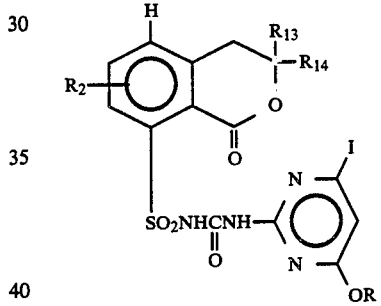
General Structure 17

TABLE 1

| | General Structure 1 | | |
|---|---|---|---|
| R | $R_1$ | $R_2$ | m.p. (°C.) |
| $CH_3$ | $CH_3$ | H | |
| $CH_3$ | $CH_2CH_3$ | H | |
| $CH_3$ | $CH_2CH_2CH_3$ | H | |
| $CH_3$ | $CH(CH_3)_2$ | H | |
| $CH_3$ | $CH(CH_3)CH_2CH_3$ | H | |
| $CH_3$ | $OCH_3$ | H | |
| $CH_3$ | $OCH_2CH_3$ | H | |
| $CH_3$ | $OCH_2CH_2CH_3$ | H | |
| $CH_3$ | $OCH(CH_3)_2$ | H | |
| $CH_3$ | $OCH_2CH_2CH_2CH_3$ | H | |
| $CH_3$ | $OCH_2CH_2OCH_3$ | H | |
| $CH_3$ | F | H | |
| $CH_3$ | Cl | H | 197–200 (dec) |
| $CH_3$ | Br | H | |
| $CH_3$ | $NO_2$ | H | 223.5–225 (dec) |
| $CH_3$ | $CF_3$ | H | 217–220 (dec) |
| $CH_3$ | $CO_2CH_3$ | H | 194–196 (dec) |
| $CH_3$ | $CO_2CH_3$ | 5-F | |
| $CH_3$ | $CO_2CH_3$ | 3-Cl | |
| $CH_3$ | $CO_2CH_3$ | 5-Cl | |
| $CH_3$ | $CO_2CH_3$ | 6-Cl | |
| $CH_3$ | $CO_2CH_3$ | 5-Br | |
| $CH_3$ | $CO_2CH_3$ | 5-$CF_3$ | 148–150 |
| $CH_3$ | $CO_2CH_3$ | 5-$CH_3$ | 185–187 |
| $CH_3$ | $CO_2CH_3$ | 5-$OCH_3$ | 195–197 |
| $CH_3$ | $CO_2CH_3$ | 5-$OCH_2CH_3$ | |
| $CH_3$ | $CO_2CH_3$ | 5-$SCH_3$ | |
| $CH_3$ | $CO_2CH_3$ | 5-$OCF_2H$ | |

TABLE 1-continued

General Structure 1

| R | $R_1$ | $R_2$ | m.p. (°C.) |
|---|---|---|---|
| $CH_3$ | $CO_2CH_3$ | 3-$CH_3$ | |
| $CH_3$ | $CO_2CH_2CH_3$ | H | 186–187.5 (dec) |
| $CH_3$ | $CO_2CH_2CH_3$ | 3-Cl | |
| $CH_3$ | $CO_2CH_2CH_3$ | 5-Cl | |
| $CH_3$ | $CO_2CH_2CH_3$ | 6-Cl | |
| $CH_3$ | $CO_2CH_2CH_3$ | 5-$CF_3$ | |
| $CH_3$ | $CO_2CH_2CH_3$ | 3-$CH_3$ | |
| $CH_3$ | $CO_2CH_2CH_3$ | 5-$CH_3$ | |
| $CH_3$ | $CO_2CH_2CH_3$ | 5-$OCH_3$ | |
| $CH_3$ | $CO_2CH_2CH_3$ | 5-$SCH_3$ | |
| $CH_3$ | $CO_2CH_2CH_3$ | 5-$OCF_2H$ | |
| $CH_3$ | $CO_2CH_2CH_3$ | 5-$OCH_2CH_3$ | |
| $CH_3$ | $CO_2CH(CH_3)_2$ | 3-Cl | |
| $CH_3$ | $CO_2CH(CH_3)_2$ | 5-Cl | |
| $CH_3$ | $CO_2CH(CH_3)_2$ | 6-Cl | |
| $CH_3$ | $CO_2CH(CH_3)_2$ | 5-$CF_3$ | |
| $CH_3$ | $CO_2CH(CH_3)_2$ | 3-$CH_3$ | |
| $CH_3$ | $CO_2CH(CH_3)_2$ | 5-$CH_3$ | |
| $CH_3$ | $CO_2CH(CH_3)_2$ | 5-$OCH_3$ | |
| $CH_3$ | $CO_2CH(CH_3)_2$ | 5-$OCF_2H$ | |
| $CH_3$ | $CO_2CH_2CH_2CH_3$ | H | |
| $CH_3$ | $CO_2CH_2CH_2CH_3$ | 5-$OCH_3$ | |
| $CH_3$ | $CO_2CH_2CH_2CH_3$ | 5-$CH_3$ | |
| $CH_3$ | $CO_2CH_2CH(CH_3)_2$ | H | |
| $CH_3$ | $CO_2CH(CH_3)CH_2CH_3$ | H | |
| $CH_3$ | $CO_2CH_2CH_2CH_2CH_3$ | H | |
| $CH_3$ | $CO_2CH_2CH_2OCH_3$ | H | |
| $CH_3$ | $CO_2CH_2CH_2OCH_3$ | 5-$CF_3$ | |
| $CH_3$ | $CO_2CH_2CH_2OCH_3$ | 5-Cl | |
| $CH_3$ | $CO_2CH_2CH_2OCH_3$ | 5-$OCH_3$ | |
| $CH_3$ | $CO_2CH_2CH_2Cl$ | 5-$CH_3$ | |
| $CH_3$ | $CO_2CH_2CH_2Cl$ | H | |
| $CH_3$ | $CO_2CH_2CH_2Cl$ | 5-$OCH_3$ | |
| $CH_3$ | $CO_2CH_2CH=CH_2$ | H | |
| $CH_3$ | $CO_2CH_2CH=CH_2$ | 5-$CF_3$ | |
| $CH_3$ | $CO_2CH_2CH=CH_2$ | 5-$OCH_3$ | |
| $CH_3$ | $SO_2N(CH_3)_2$ | H | 231–232.5 (dec) |
| $CH_3$ | $SO_2N(CH_3)_2$ | 3-Cl | |
| $CH_3$ | $SO_2N(CH_3)CH_2CH_3$ | H | |
| $CH_3$ | $SO_2N(CH_2CH_3)_2$ | H | |
| $CH_3$ | $SO_2N(CH_3)CH(CH_3)_2$ | H | |
| $CH_3$ | $SO_2N(CH_3)CH_2CH_2CH_3$ | H | |
| $CH_3$ | $OSO_2CH_3$ | H | 217–219 (dec) |
| $CH_3$ | $OSO_2CH_3$ | 5-Cl | |
| $CH_3$ | $OSO_2CH_2CH_3$ | H | |
| $CH_3$ | $OSO_2CH(CH_3)_2$ | H | |
| $CH_3$ | $OSO_2CH_2CH_2CH_3$ | H | |
| $CH_3$ | $OSO_2N(CH_3)_2$ | H | |
| $CH_3$ | $SCH_3$ | H | 116–120 |
| $CH_3$ | $SCH_2CH_3$ | H | |
| $CH_3$ | $SCH_2CH_2CH_3$ | H | |
| $CH_3$ | $SCH(CH_3)_2$ | H | |
| $CH_3$ | $SCH_2CH=CH_2$ | H | |
| $CH_3$ | $SOCH_3$ | H | |
| $CH_3$ | $SOCH_2CH_3$ | H | |
| $CH_3$ | $SO_2CH_3$ | H | 239–241 (dec) |
| $CH_3$ | $SO_2CH_2CH_3$ | H | |
| $CH_3$ | $SO_2CH_2CH_2CH_3$ | H | |
| $CH_3$ | $SO_2CH(CH_3)_2$ | H | |
| $CH_3$ | $SO_2CH_2CH=CH_2$ | H | |
| $CH_3$ | $SCF_3$ | H | |
| $CH_3$ | $SO_2CF_3$ | H | |
| $CH_3$ | $OCF_3$ | H | |
| $CH_3$ | $SCF_2H$ | H | |
| $CH_3$ | $SO_2CF_2H$ | H | |
| $CH_3$ | $OCF_2H$ | H | |
| $CH_3$ | $OCH_2CH=CH_2$ | H | |
| $CH_3$ | $OCH_2CH=CHCH_3$ | H | |
| $CH_3$ | $OCH(CH_3)CH=CH_2$ | H | |
| $CH_3$ | $OCH_2C\equiv CH$ | H | |
| $CH_3$ | $OCH_2C\equiv CCH_3$ | H | |
| $CH_3$ | $OCH(CH_3)C\equiv CH$ | H | |
| $CH_3$ | $CH_2OCH_3$ | H | |
| $CH_3$ | $CH_2OCH_2CH_3$ | H | |
| $CH_3$ | $CH_2CH_2OCH_3$ | H | |
| $CH_3$ | $CH(CH_3)OCH_3$ | H | |
| $CH_3$ | $C_6H_5$ | H | |

TABLE 1-continued

General Structure 1

| R | R₁ | R₂ | m.p. (°C.) |
|---|---|---|---|
| CH₃ | 3,5-dimethyl-1,2,4-oxadiazol-yl (N—N, O, two CH₃) | H | |
| CH₃ | 5-methyl-1,3,4-oxadiazol-2-yl | H | |
| CH₃ | 5-methylisoxazol-3-yl (O-N) | H | |
| CH₃ | 3-methylisoxazol-5-yl (N-O) | H | |
| CH₃ | 4-methyl-1,2,3-thiadiazol-5-yl (N=N, S) | H | |
| CH₃ | 4-methyl-1,2,3-thiadiazol-5-yl | 5-Cl | |
| CH₃ | 5-methylisoxazol-4-yl | H | |
| CH₃ | 1,5-dimethylpyrazol-3-yl (N-NCH₃) | H | |
| CH₃ | 5-methyloxazol-4-yl (N, O) | H | |
| CH₃ | 1-methylpyrazol-3-yl | H | |
| CH₃ | 1,2,4-triazol-3-yl | H | |
| CH₃ | 5-methyltetrahydrofuran-2-yl | H | |
| CH₃ | 5-methylfuran-2-yl | H | |
| CH₃ | 5-methylthiophen-2-yl | H | |
| CH₃ | 6-methylpyridin-2-yl | H | |

TABLE 1-continued

General Structure 1

| R | R₁ | R₂ | m.p. (°C.) |
|---|---|---|---|
| CH₃ | 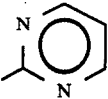 | H | |
| CH₂CH₃ | CH₃ | H | |
| CH₂CH₃ | CH₂CH₃ | H | |
| CH₂CH₃ | CH₂CH₂CH₃ | H | |
| CH₂CH₃ | CH(CH₃)₂ | H | |
| CH₂CH₃ | CH(CH₃)CH₂CH₃ | H | |
| CH₂CH₃ | OCH₃ | H | |
| CH₂CH₃ | OCH₂CH₃ | H | |
| CH₂CH₃ | OCH₂CH₂CH₃ | H | |
| CH₂CH₃ | OCH(CH₃)₂ | H | |
| CH₂CH₃ | OCH₂CH₂CH₂CH₃ | H | |
| CH₂CH₃ | OCH₂CH₂OCH₃ | H | |
| CH₂CH₃ | F | H | |
| CH₂CH₃ | Cl | H | |
| CH₂CH₃ | Br | H | |
| CH₂CH₃ | NO₂ | H | |
| CH₂CH₃ | CF₃ | H | |
| CH₂CH₃ | CO₂CH₃ | H | |
| CH₂CH₃ | CO₂CH₃ | 5-F | |
| CH₂CH₃ | CO₂CH₃ | 3-Cl | |
| CH₂CH₃ | CO₂CH₃ | 5-Cl | |
| CH₂CH₃ | CO₂CH₃ | 6-Cl | |
| CH₂CH₃ | CO₂CH₃ | 5-Br | |
| CH₂CH₃ | CO₂CH₃ | 5-CF₃ | |
| CH₂CH₃ | CO₂CH₃ | 5-CH₃ | |
| CH₂CH₃ | CO₂CH₃ | 5-OCH₃ | |
| CH₂CH₃ | CO₂CH₃ | 5-OCH₂CH₃ | |
| CH₂CH₃ | CO₂CH₃ | 5-SCH₃ | |
| CH₂CH₃ | CO₂CH₃ | 5-OCF₂H | |
| CH₂CH₃ | CO₂CH₃ | 3-CH₃ | |
| CH₂CH₃ | CO₂CH₂CH₃ | H | |
| CH₂CH₃ | CO₂CH₂CH₃ | 3-Cl | |
| CH₂CH₃ | CO₂CH₂CH₃ | 5-Cl | |
| CH₂CH₃ | CO₂CH₂CH₃ | 6-Cl | |
| CH₂CH₃ | CO₂CH₂CH₃ | 5-CF₃ | |
| CH₂CH₃ | CO₂CH₂CH₃ | 3-CH₃ | |
| CH₂CH₃ | CO₂CH₂CH₃ | 5-CH₃ | |
| CH₂CH₃ | CO₂CH₂CH₃ | 5-OCH₃ | |
| CH₂CH₃ | CO₂CH₂CH₃ | 5-SCH₃ | |
| CH₂CH₃ | CO₂CH₂CH₃ | 5-OCF₂H | |
| CH₂CH₃ | CO₂CH₂CH₃ | 5-OCH₂CH₃ | |
| CH₂CH₃ | CO₂CH(CH₃)₂ | 3-Cl | |
| CH₂CH₃ | CO₂CH(CH₃)₂ | 5-Cl | |
| CH₂CH₃ | CO₂CH(CH₃)₂ | 6-Cl | |
| CH₂CH₃ | CO₂CH(CH₃)₂ | 5-CF₃ | |
| CH₂CH₃ | CO₂CH(CH₃)₂ | 3-CH₃ | |
| CH₂CH₃ | CO₂CH(CH₃)₂ | 5-CH₃ | |
| CH₂CH₃ | CO₂CH(CH₃)₂ | 5-OCH₃ | |
| CH₂CH₃ | CO₂CH(CH₃)₂ | 5-OCF₂H | |
| CH₂CH₃ | CO₂CH₂CH₂CH₃ | H | |
| CH₂CH₃ | CO₂CH₂CH₂CH₃ | 5-OCH₃ | |
| CH₂CH₃ | CO₂CH₂CH₂CH₃ | 5-CH₃ | |
| CH₂CH₃ | CO₂CH₂CH(CH₃)₂ | H | |
| CH₂CH₃ | CO₂CH(CH₃)CH₂CH₃ | H | |
| CH₂CH₃ | CO₂CH₂CH₂CH₂CH₃ | H | |
| CH₂CH₃ | CO₂CH₂CH₂OCH₃ | H | |
| CH₂CH₃ | CO₂CH₂CH₂OCH₃ | 5-CF₃ | |
| CH₂CH₃ | CO₂CH₂CH₂OCH₃ | 5-Cl | |
| CH₂CH₃ | CO₂CH₂CH₂OCH₃ | 5-OCH₃ | |
| CH₂CH₃ | CO₂CH₂CH₂Cl | 5-CH₃ | |
| CH₂CH₃ | CO₂CH₂CH₂Cl | H | |
| CH₂CH₃ | CO₂CH₂CH₂Cl | 5-OCH₃ | |
| CH₂CH₃ | CO₂CH₂CH=CH₂ | H | |
| CH₂CH₃ | CO₂CH₂CH=CH₂ | 5-CF₃ | |
| CH₂CH₃ | CO₂CH₂CH=CH₂ | 5-OCH₃ | |
| CH₂CH₃ | SO₂N(CH₃)₂ | H | |
| CH₂CH₃ | SO₂N(CH₃)₂ | 3-Cl | |
| CH₂CH₃ | SO₂N(CH₃)CH₂CH₃ | H | |
| CH₂CH₃ | SO₂N(CH₂CH₃)₂ | H | |
| CH₂CH₃ | SO₂N(CH₃)CH(CH₃)₂ | H | |
| CH₂CH₃ | SO₂N(CH₃)CH₂CH₂CH₃ | H | |
| CH₂CH₃ | OSO₂CH₃ | H | |
| CH₂CH₃ | OSO₂CH₃ | 5-Cl | |
| CH₂CH₃ | OSO₂CH₂CH₃ | H | |

TABLE 1-continued

General Structure 1

| R | R₁ | R₂ | m.p. (°C.) |
|---|---|---|---|
| $CH_2CH_3$ | $OSO_2CH(CH_3)_2$ | H | |
| $CH_2CH_3$ | $OSO_2CH_2CH_2CH_3$ | H | |
| $CH_2CH_3$ | $OSO_2N(CH_3)_2$ | H | |
| $CH_2CH_3$ | $SCH_3$ | H | |
| $CH_2CH_3$ | $SCH_2CH_3$ | H | |
| $CH_2CH_3$ | $SCH_2CH_2CH_3$ | H | |
| $CH_2CH_3$ | $SCH(CH_3)_2$ | H | |
| $CH_2CH_3$ | $SCH_2CH=CH_2$ | H | |
| $CH_2CH_3$ | $SOCH_3$ | H | |
| $CH_2CH_3$ | $SOCH_2CH_3$ | H | |
| $CH_2CH_3$ | $SO_2CH_3$ | H | |
| $CH_2CH_3$ | $SO_2CH_2CH_3$ | H | |
| $CH_2CH_3$ | $SO_2CH_2CH_2CH_3$ | H | |
| $CH_2CH_3$ | $SO_2CH(CH_3)_2$ | H | |
| $CH_2CH_3$ | $SO_2CH_2CH=CH_2$ | H | |
| $CH_2CH_3$ | $SCF_3$ | H | |
| $CH_2CH_3$ | $SO_2CF_3$ | H | |
| $CH_2CH_3$ | $OCF_3$ | H | |
| $CH_2CH_3$ | $SCF_2H$ | H | |
| $CH_2CH_3$ | $SO_2CF_2H$ | H | |
| $CH_2CH_3$ | $OCF_2H$ | H | |
| $CH_2CH_3$ | $OCH_2CH=CH_2$ | H | |
| $CH_2CH_3$ | $OCH_2CH=CHCH_3$ | H | |
| $CH_2CH_3$ | $OCH(CH_3)CH=CH_2$ | H | |
| $CH_2CH_3$ | $OCH_2C\equiv CH$ | H | |
| $CH_2CH_3$ | $OCH_2C\equiv CCH_3$ | H | |
| $CH_2CH_3$ | $OCH(CH_3)C\equiv CH$ | H | |
| $CH_2CH_3$ | $CH_2OCH_3$ | H | |
| $CH_2CH_3$ | $CH_2OCH_2CH_3$ | H | |
| $CH_2CH_3$ | $CH_2CH_2OCH_3$ | H | |
| $CH_2CH_3$ | $CH(CH_3)OCH_3$ | H | |
| $CH_2CH_3$ | $C_6H_5$ | H | |
| $CH_2CH_3$ | 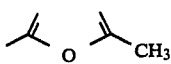 | H | |
| $CH_2CH_3$ | 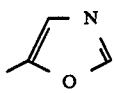 | H | |
| $CH_2CH_3$ | 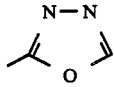 | H | |
| $CH_2CH_3$ | 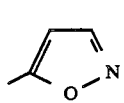 | H | |
| $CH_2CH_3$ | 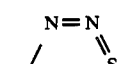 | H | |
| $CH_2CH_3$ | 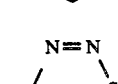 | H | |
| $CH_2CH_3$ | 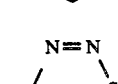 | 5-Cl | |
| $CH_2CH_3$ | 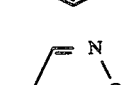 | H | |
| $CH_2CH_3$ | 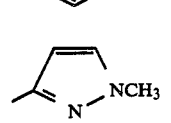 | H | |

TABLE 1-continued

General Structure 1

| R | R₁ | R₂ | m.p. (°C.) |
|---|---|---|---|
| CH₂CH₃ | 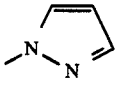 | H | |
| CH₂CH₃ | 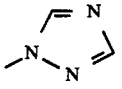 | H | |
| CH₂CH₃ | 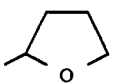 | H | |
| CH₂CH₃ | 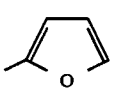 | H | |
| CH₂CH₃ |  | H | |
| CH₂CH₃ |  | H | |
| CH₂CH₃ | 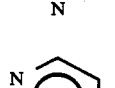 | H | |
| CH₂CH₃ | 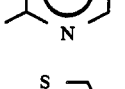 | H | |
| CH₂CH₃ | 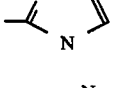 | H | |
| CH₃ | CO₂CH₃ | 5-CH₂CH₃ | |
| CH₃ | CO₂CH₃ | 5-CH₂CH₂CH₂CH₃ | |
| CH₃ | CO₂CH₃ | 5-OCH₂CH₂CH₂CH₃ | |
| CH₃ | CO₂CH₃ | 5-OCH₂CH=CH₂ | |
| CH₃ | CO₂CH₃ | 5-OCH₂C≡CH | |
| CH₃ | CO₂CH₃ | 5-OCH₂CHClCH₂CH₃ | |
| CH₃ | CO₂CH₃ | 5-SOCH₃ | |
| CH₃ | CO₂CH₃ | 5-SCH₂CH=CH₂ | |
| CH₃ | CO₂CH₃ | 5-SCH₂C≡CH | |
| CH₃ | CO₂CH₃ | 5-SCH₂CH₂C≡CH | |
| CH₃ | CO₂CH₃ | 5-CH₂OCH₃ | |
| CH₃ | CO₂CH₃ | 5-CH₂SCH₃ | |
| CH₃ | CO₂CH₃ | 5-CH₂CH₂CH₃ | |
| CH₃ | CO₂CH₃ | 5-OCH₂CH₂CH₃ | |
| CH₃ | CO₂CH₃ | 5-OCH₂CH₂CH=CH₂ | |
| CH₃ | CO₂CH₃ | 5-OCH₂CH₂C≡CH | |
| CH₃ | CO₂CH₃ | 5-OCF₂CF₂H | |
| CH₃ | CO₂CH₃ | 5-SO₂CH₃ | |
| CH₃ | CO₂CH₃ | 5-SCH₂CH₂CH=CH₂ | |
| CH₃ | CO₂CH₃ | 5-CH₂CH₂OCH₃ | |
| CH₃ | CO₂CH₃ | 5-SO₂CH₂CH₃ | |
| CH₃ | CO₂CH₃ | 5-SO₂CH₂CH₂CH₂CH₃ | |
| CH₃ | CO₂CH₃ | 5-SO₂CH₂CH=CH₂ | |
| CH₃ | CO₂CH₃ | 5-SO₂CH₂C≡CH | |
| CH₃ | C(O)CH₃ | H | |
| CH₃ | C(CH₃)(OCH₃)₂ | H | |
| CH₃ | SO₂NHCH₃ | H | |

TABLE 2

General Structure 2

| R | $R_3$ | m.p. (°C.) |
|---|---|---|
| $CH_3$ | $CH_3$ | |
| $CH_2CH_3$ | $CH_3$ | |
| $CH_3$ | $OCH_3$ | |
| $CH_2CH_3$ | $OCH_3$ | |
| $CH_3$ | F | |
| $CH_3$ | H | |
| $CH_3$ | Cl | |
| $CH_2CH_3$ | Cl | |
| $CH_3$ | Br | |
| $CH_2CH_3$ | Br | |
| $CH_3$ | $SO_2N(CH_3)_2$ | |
| $CH_3$ | $OSO_2CH_3$ | |
| $CH_3$ | $SCH_3$ | |
| $CH_3$ | $SOCH_3$ | |
| $CH_3$ | $SO_2CH_3$ | |

TABLE 3

General Structure 3

| R | $R_4$ | m.p. (°C.) |
|---|---|---|
| $CH_3$ | $CH_3$ | |
| $CH_3$ | $CH_2CH_3$ | |
| $CH_3$ | $OCH_3$ | |
| $CH_2CH_3$ | $OCH_3$ | |
| $CH_3$ | $OCH_2CH_3$ | |
| $CH_3$ | F | |
| $CH_3$ | Cl | |
| $CH_2CH_3$ | Cl | |
| $CH_3$ | Br | |
| $CH_3$ | $SO_2N(CH_3)_2$ | |
| $CH_3$ | $SO_2N(CH_2CH_3)_2$ | |
| $CH_3$ | $SO_2N(OCH_3)CH_3$ | |
| $CH_3$ | $SO_2CH_3$ | |
| $CH_3$ | $SCH_3$ | |
| $CH_3$ | $SOCH_3$ | |
| $CH_3$ | $SCH_2CH_3$ | |
| $CH_3$ | $SO_2CH_2CH_3$ | |
| $CH_3$ | $SO_2CH_2CH(CH_3)_2$ | |
| $CH_3$ | $SO_2CH_2CH_2CH_3$ | |
| $CH_3$ | $SCH_2CH=CH_2$ | |
| $CH_3$ | $SO_2CH_2CH=CH_2$ | |
| $CH_3$ | $OCH_2CH=CH_2$ | |
| $CH_2CH_3$ | $OCH_2CH=CH_2$ | |
| $CH_3$ | $OCH(CH_3)CH=CH_2$ | |
| $CH_3$ | $OCH_2C\equiv CH$ | |
| $CH_3$ | $OCH_2C\equiv CCH_3$ | |

TABLE 4

General Structure 4

| R | $R_5$ | $R_{20}$ | m.p. (°C.) |
|---|---|---|---|
| $CH_3$ | $CH_3$ | H | |
| $CH_3$ | $CH_2CH_3$ | H | |
| $CH_3$ | $CH_2CH_2CH_3$ | H | |
| $CH_3$ | $CH(CH_3)_2$ | 5-Cl | |
| $CH_3$ | F | H | |
| $CH_3$ | Cl | H | |
| $CH_3$ | Br | H | |
| $CH_3$ | $NO_2$ | H | |
| $CH_3$ | $CO_2CH_3$ | H | |
| $CH_3$ | $CO_2CH_2CH_3$ | H | |
| $CH_3$ | $CO_2CH(CH_3)_2$ | H | |
| $CH_3$ | $CO_2CH_2CH_2CH_3$ | H | |
| $CH_3$ | $CO_2CH(CH_3)CH_2CH_3$ | H | |
| $CH_3$ | $CO_2CH_2CH_2OCH_3$ | H | |
| $CH_3$ | $CO_2CH_2CH_2Cl$ | H | |
| $CH_3$ | $CO_2CH_2CH=CH_2$ | H | |
| $CH_2CH_3$ | $CO_2CH_3$ | H | |
| $CH_2CH_3$ | $CO_2CH_2CH_3$ | 5-$CH_3$ | |
| $CH_3$ | $SO_2N(CH_3)_2$ | H | |
| $CH_3$ | $SO_2N(CH_2CH_3)_2$ | H | |
| $CH_3$ | $SO_2N(OCH_3)CH_3$ | H | |
| $CH_3$ | $SCH_3$ | H | |
| $CH_3$ | $SOCH_3$ | H | |
| $CH_3$ | $SO_2CH_3$ | H | |
| $CH_3$ | $SCH_2CH_3$ | H | |
| $CH_3$ | $SCH_2CH_2CH_3$ | H | |
| $CH_3$ | $SCH_2CH=CH_2$ | H | |

TABLE 5

General Structure 5

| R | $R_5$ | $R_{20}$ | m.p. (°C.) |
|---|---|---|---|
| $CH_3$ | $CH_3$ | H | |
| $CH_3$ | $CH_2CH_3$ | H | |
| $CH_3$ | $CH_2CH_2CH_3$ | H | |
| $CH_3$ | $CH(CH_3)_2$ | 5-Cl | |
| $CH_3$ | F | H | |
| $CH_3$ | Cl | H | |
| $CH_3$ | Br | H | |
| $CH_3$ | $NO_2$ | H | |
| $CH_3$ | $CO_2CH_3$ | H | |
| $CH_3$ | $CO_2CH_2CH_3$ | H | |
| $CH_3$ | $CO_2CH(CH_3)_2$ | H | |
| $CH_3$ | $CO_2CH_2CH_2CH_3$ | H | |
| $CH_3$ | $CO_2CH(CH_3)CH_2CH_3$ | H | |
| $CH_3$ | $CO_2CH_2CH_2OCH_3$ | H | |
| $CH_3$ | $CO_2CH_2CH_2Cl$ | H | |
| $CH_3$ | $CO_2CH_2CH=CH_2$ | H | |
| $CH_2CH_3$ | $CO_2CH_3$ | H | |
| $CH_2CH_3$ | $CO_2CH_2CH_3$ | 5-$CH_3$ | |
| $CH_3$ | $SO_2N(CH_3)_2$ | H | |
| $CH_3$ | $SO_2N(CH_2CH_3)_2$ | H | |
| $CH_3$ | $SO_2N(OCH_3)CH_3$ | H | |
| $CH_3$ | $SCH_3$ | H | |
| $CH_3$ | $SOCH_3$ | H | |
| $CH_3$ | $SO_2CH_3$ | H | |
| $CH_3$ | $SCH_2CH_3$ | H | |
| $CH_3$ | $SCH_2CH_2CH_3$ | H | |
| $CH_3$ | $SCH_2CH=CH_2$ | H | |

TABLE 6

General Structure 6

| R | $R_5$ | $R_{20}$ | m.p. (°C.) |
|---|---|---|---|
| $CH_3$ | $CH_3$ | H | |
| $CH_3$ | $CH_2CH_3$ | H | |
| $CH_3$ | $CH_2CH_2CH_3$ | H | |
| $CH_3$ | $CH(CH_3)_2$ | 2-Cl | |
| $CH_3$ | F | H | |
| $CH_3$ | Cl | H | |
| $CH_3$ | Br | H | |
| $CH_3$ | $NO_2$ | H | |
| $CH_3$ | $CO_2CH_3$ | H | |
| $CH_3$ | $CO_2CH_2CH_3$ | H | |
| $CH_3$ | $CO_2CH(CH_3)_2$ | H | |
| $CH_3$ | $CO_2CH_2CH_2CH_3$ | H | |
| $CH_3$ | $CO_2CH(CH_3)CH_2CH_3$ | H | |
| $CH_3$ | $CO_2CH_2CH_2OCH_3$ | H | |
| $CH_3$ | $CO_2CH_2CH_2Cl$ | H | |
| $CH_3$ | $CO_2CH_2CH=CH_2$ | H | |
| $CH_2CH_3$ | $CO_2CH_3$ | H | |
| $CH_2CH_3$ | $CO_2CH_2CH_3$ | 2-$CH_3$ | |
| $CH_3$ | $SO_2N(CH_3)_2$ | H | |
| $CH_3$ | $SO_2N(CH_2CH_3)_2$ | H | |
| $CH_3$ | $SO_2N(OCH_3)CH_3$ | H | |
| $CH_3$ | $SCH_3$ | H | |
| $CH_3$ | $SOCH_3$ | H | |
| $CH_3$ | $SO_2CH_3$ | H | |
| $CH_3$ | $SCH_2CH_3$ | H | |
| $CH_3$ | $SCH_2CH_2CH_3$ | H | |
| $CH_3$ | $SCH_2CH=CH_2$ | H | |

TABLE 7

General Structure 7

| R | $R_6$ | m.p. (°C.) |
|---|---|---|
| $CH_3$ | Cl | |
| $CH_3$ | $NO_2$ | |
| $CH_3$ | $CO_2CH_3$ | |

TABLE 7-continued

General Structure 7

| R | R$_6$ | m.p. (°C.) |
|---|---|---|
| CH$_2$CH$_3$ | CO$_2$CH$_3$ | |
| CH$_3$ | CO$_2$CH$_2$CH$_3$ | |
| CH$_2$CH$_3$ | CO$_2$CH$_2$CH$_3$ | |
| CH$_3$ | SO$_2$N(CH$_3$)$_2$ | |
| CH$_3$ | OSO$_2$CH$_3$ | |
| CH$_3$ | SO$_2$CH$_3$ | |
| CH$_3$ | SO$_2$CH$_2$CH$_3$ | |
| CH$_3$ | OCH$_3$ | |
| CH$_3$ | OCH$_2$CH$_3$ | |

TABLE 8

General Structure 8

| R | R$_2$ | R$_7$ | R$_8$ | R$_9$ | m | Q$_1$ | m.p. (°C.) |
|---|---|---|---|---|---|---|---|
| CH$_3$ | H | H | H | H | 0 | O | |
| CH$_3$ | H | CH$_3$ | H | H | 0 | O | |
| CH$_3$ | H | CH$_3$ | CH$_3$ | H | 0 | O | |
| CH$_3$ | H | H | H | CH$_3$ | 0 | O | |
| CH$_3$ | H | H | CH$_3$ | H | 1 | O | |
| CH$_3$ | H | CH$_3$ | CH$_3$ | H | 1 | O | |
| CH$_3$ | H | CH$_3$ | H | H | 0 | S | |
| CH$_3$ | H | CH$_3$ | CH$_3$ | H | 0 | S | |
| CH$_3$ | H | H | H | CH$_3$ | 0 | S | |
| CH$_3$ | H | CH$_3$ | H | H | 1 | S | |
| CH$_3$ | H | CH$_3$ | CH$_3$ | H | 1 | S | |
| CH$_3$ | H | H | H | H | 0 | SO$_2$ | |
| CH$_3$ | H | CH$_3$ | H | H | 0 | SO$_2$ | |
| CH$_2$CH$_3$ | H | CH$_3$ | H | H | 0 | SO$_2$ | |
| CH$_3$ | H | CH$_3$ | CH$_3$ | H | 0 | SO$_2$ | |
| CH$_2$CH$_3$ | H | CH$_3$ | CH$_3$ | H | 0 | SO$_2$ | |
| CH$_3$ | H | CH$_3$ | H | CH$_3$ | 0 | SO$_2$ | |
| CH$_3$ | H | CH$_3$ | H | H | 1 | SO$_2$ | |
| CH$_3$ | H | CH$_3$ | CH$_3$ | H | 1 | SO$_2$ | |
| CH$_3$ | H | CH$_2$CH$_3$ | H | H | 0 | SO$_2$ | |
| CH$_3$ | H | CH$_2$CH$_3$ | H | H | 1 | SO$_2$ | |
| CH$_3$ | 6-Cl | CH$_3$ | H | H | 0 | SO$_2$ | |
| CH$_3$ | 7-Cl | CH$_3$ | H | H | 1 | SO$_2$ | |
| CH$_3$ | 5-Br | CH$_3$ | H | H | 0 | O | |
| CH$_3$ | 6-CH$_3$ | CH$_3$ | H | H | 0 | SO$_2$ | |
| CH$_3$ | 7-Cl | CH$_3$ | H | H | 1 | S | |
| CH$_3$ | 6-Cl | CH$_3$ | H | H | 0 | SO$_2$ | |

TABLE 9

General Structure 9

| R | R$_2$ | R$_{10}$ | R$_{11}$ | Q$_2$ | m.p. (°C.) |
|---|---|---|---|---|---|
| CH$_3$ | H | H | H | O | |
| CH$_3$ | H | CH$_3$ | H | O | |
| CH$_3$ | H | CH$_3$ | CH$_3$ | O | |
| CH$_2$CH$_3$ | H | H | H | O | |
| CH$_2$CH$_3$ | H | CH$_3$ | H | O | |
| CH$_2$CH$_3$ | H | CH$_3$ | CH$_3$ | O | |
| CH$_3$ | H | H | H | S | |
| CH$_3$ | H | CH$_3$ | H | S | |
| CH$_3$ | H | CH$_3$ | CH$_3$ | S | |
| CH$_2$CH$_3$ | H | H | H | S | |
| CH$_2$CH$_3$ | H | CH$_3$ | H | S | |
| CH$_2$CH$_3$ | H | CH$_3$ | CH$_3$ | S | |

TABLE 10

General Structure 10

| R | R$_2$ | R$_9$ | R$_{12}$ | m | m.p. (°C.) |
|---|---|---|---|---|---|
| CH$_3$ | H | H | CH$_3$ | 0 | |
| CH$_3$ | H | CH$_3$ | CH$_3$ | 0 | |
| CH$_3$ | H | H | CH$_3$ | 1 | |
| CH$_2$CH$_3$ | H | H | CH$_3$ | 0 | |
| CH$_2$CH$_3$ | H | CH$_3$ | CH$_3$ | 0 | |
| CH$_2$CH$_3$ | H | H | CH$_3$ | 1 | |
| CH$_3$ | H | H | CH$_2$CH$_3$ | 0 | |
| CH$_3$ | H | H | CH$_2$CH$_2$CH$_3$ | 0 | |
| CH$_3$ | H | H | CH(CH$_3$)$_2$ | 0 | |
| CH$_3$ | H | H | CH$_2$CH$_2$CH$_2$CH$_3$ | 0 | |
| CH$_3$ | H | H | CH(CH$_3$)CH$_2$CH$_3$ | 0 | |

TABLE 10-continued

General Structure 10

| R | R$_2$ | R$_9$ | R$_{12}$ | m | m.p. (°C.) |
|---|---|---|---|---|---|
| CH$_3$ | H | H | CH$_2$CH(CH$_3$)$_2$ | 0 | |
| CH$_3$ | H | H | CH$_2$CH$_3$ | 1 | |
| CH$_3$ | H | H | CH(CH$_3$)$_2$ | 1 | |
| CH$_3$ | H | H | CH$_2$CH$_2$CH$_3$ | 1 | |
| CH$_3$ | 6-Cl | H | CH$_3$ | 0 | |
| CH$_3$ | H | H | CH$_2$CH$_2$F | 0 | |
| CH$_3$ | H | H | CH$_2$CH$_2$OCH$_3$ | 0 | |
| CH$_3$ | H | H | CH$_2$CH=CH$_2$ | 0 | |
| CH$_3$ | H | H | CH$_2$C≡CH | 0 | |
| CH$_3$ | H | H | CH$_2$C$_6$H$_5$ | 0 | |
| CH$_3$ | H | H | C(O)CH$_3$ | 0 | |
| CH$_3$ | H | H | C(O)CH$_2$CH$_2$CH$_3$ | 1 | |
| CH$_3$ | H | H | CO$_2$CH$_3$ | 0 | |
| CH$_3$ | H | H | CH$_2$CN | 0 | |
| CH$_3$ | H | H | CH$_2$C(O)CH$_3$ | 0 | |
| CH$_3$ | H | H | CH$_2$CO$_2$CH$_3$ | 0 | |
| CH$_3$ | H | H | CH$_2$CF=CF$_2$ | 1 | |
| CH$_3$ | H | H | CH$_2$CH=CCL$_2$ | 0 | |
| CH$_3$ | H | H | CH$_2$CH$_2$F | 0 | |
| CH$_3$ | H | H | CH$_2$OCH$_3$ | 0 | |

TABLE 11

General Structure 11

| R | R$_2$ | R$_9$ | m | m.p. (°C.) |
|---|---|---|---|---|
| CH$_3$ | H | H | 0 | |
| CH$_3$ | H | CH$_3$ | 0 | |
| CH$_3$ | H | H | 1 | 183–186 |
| CH$_2$CH$_3$ | H | H | 0 | |
| CH$_2$CH$_3$ | H | CH$_3$ | 0 | |
| CH$_2$CH$_3$ | H | H | 1 | |
| CH$_3$ | 6-Cl | H | 0 | |
| CH$_3$ | 7-Cl | H | 1 | |
| CH$_3$ | 6-Cl | H | 1 | |
| CH$_3$ | 6-CH$_3$ | H | 1 | |

TABLE 12

General Structure 12

| R | R$_2$ | R$_9$ | m | m.p. (°C.) |
|---|---|---|---|---|
| CH$_3$ | H | H | 0 | |
| CH$_3$ | H | CH$_3$ | 0 | |
| CH$_3$ | H | H | 1 | |
| CH$_2$CH$_3$ | H | H | 0 | |
| CH$_2$CH$_3$ | H | CH$_3$ | 0 | |
| CH$_2$CH$_3$ | H | H | 1 | |

TABLE 13

General Structure 13

| R | R$_2$ | R$_9$ | m | m.p. (°C.) |
|---|---|---|---|---|
| CH$_3$ | H | H | 0 | |
| CH$_3$ | H | CH$_3$ | 0 | |
| CH$_3$ | H | H | 1 | |
| CH$_2$CH$_3$ | H | H | 0 | |
| CH$_2$CH$_3$ | H | CH$_3$ | 0 | |
| CH$_2$CH$_3$ | H | H | 1 | |

TABLE 14

General Structure 14

| R | R$_2$ | R$_{12}$ | m.p. (°C.) |
|---|---|---|---|
| CH$_3$ | H | CH$_3$ | |
| CH$_2$CH$_3$ | H | CH$_3$ | |
| CH$_3$ | H | CH$_2$CH$_3$ | |
| CH$_2$CH$_3$ | H | CH$_2$CH$_3$ | |
| CH$_3$ | H | CH$_2$CH$_2$CH$_3$ | |
| CH$_3$ | H | CH(CH$_3$)$_2$ | |
| CH$_3$ | H | CH$_2$CH$_2$CH$_2$CH$_3$ | |
| CH$_3$ | H | CH(CH$_3$)CH$_2$CH$_3$ | |
| CH$_3$ | H | CH$_2$CH(CH$_3$)$_2$ | |

TABLE 15

| R | General Structure 15 | | m.p. (°C.) |
|---|---|---|---|
|  | $R_2$ | $R_{13}$ |  |
| $CH_3$ | H | H |  |
| $CH_3$ | H | $CH_3$ |  |
| $CH_2CH_3$ | H | H |  |
| $CH_2CH_3$ | H | $CH_3$ |  |

TABLE 16

| R | General Structure 16 | | m.p. (°C.) |
|---|---|---|---|
|  | $R_2$ | $R_{13}$ |  |
| $CH_3$ | H | H |  |
| $CH_3$ | H | $CH_3$ |  |
| $CH_2CH_3$ | H | H |  |
| $CH_2CH_3$ | H | $CH_3$ |  |

TABLE 17

| R | General Structure 17 | | | m.p. (°C.) |
|---|---|---|---|---|
|  | $R_2$ | $R_{13}$ | $R_{14}$ |  |
| $CH_3$ | H | H | $CH_3$ |  |
| $CH_3$ | H | H | $CH_2CH_3$ |  |
| $CH_3$ | H | $CH_3$ | $CH_3$ |  |
| $CH_3$ | H | $CH_3$ | $CH_2CH_3$ |  |
| $CH_2CH_3$ | H | H | $CH_3$ |  |
| $CH_2CH_3$ | H | H | $CH_2CH_3$ |  |
| $CH_2CH_3$ | H | $CH_3$ | $CH_3$ |  |
| $CH_2CH_3$ | H | $CH_3$ | $CH_2CH_3$ |  |
| $CH_3$ | 6-Cl | H | $CH_3$ |  |
| $CH_3$ | 6-$CH_3$ | H | $CH_3$ |  |
| $CH_3$ | 6-Cl | $CH_3$ | $CH_3$ |  |
| $CH_3$ | 7-Cl | H | $CH_3$ |  |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further information. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 18

|  | Active Ingredient | Weight Percent* | |
|---|---|---|---|
|  |  | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See. J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 3

Wettable Powder

| | |
|---|---|
| 2-[[(4-iodo-6-methoxypyrimidin-2-yl)aminocarbonyl]-aminosulfonyl]benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 4

Wettable Powder

| | |
|---|---|
| 2-[[(4-iodo-6-methoxypyrimidin-2-yl)aminocarbonyl]-aminosulfonyl]benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 5

Granule

| | |
|---|---|
| Wettable Powder of Example 3 | 5% |
| attapulgite granules (U.S.S. 20–40 mesh; 0.84-0.42 mm) | 95% |

A slurry of wettable powder containing 25% solids is sprayed on the surface of attapulgite granules while tumbling in a double-cone blender. The granules are dried and packaged.

EXAMPLE 6

Extruded Pellet

| | |
|---|---|
| 2-[[(4-iodo-6-methoxypyrimidin-2-yl)aminocarbonyl]-aminosulfonyl]benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

Oil Suspension

| | |
|---|---|
| 2-[[(4-iodo-6-methoxypyrimidin-2-yl)aminocarbonyl]-aminosulfonyl]benzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 8

Wettable Powder

| | |
|---|---|
| N'—[(4-iodo-6-methoxypyrimidin-2-yl)aminocarbonyl]-N,N—dimethyl-1,2-benzenedisulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding a hammer-mill to produce particles essentially all below 100 microns, the material is reblended and sifted through a U.S.S. No. 50 sieve (0.3 mm opening) and packaged.

EXAMPLE 9

Low Strength Granule

| | |
|---|---|
| 2-[[(4-iodo-6-methoxypyrimidin-2-yl)aminocarbonyl]-aminosulfonyl]benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 10

Aqueous Suspension

| | |
|---|---|
| 2-[[(4-iodo-6-methoxypyrimidin-2-yl)aminocarbonyl]-aminosulfonyl]benzoic acid, methyl ester | 40% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 11

Solution

| | |
|---|---|
| 2-[[(4-iodo-6-methoxypyrimidin-2-yl)aminocarbonyl]-aminosulfonyl]benzoic acid, methyl ester, sodium salt | 5% |
| water | 95% |

The salt is added directly to the water with stirring to produce the solution, which may then be packaged for use.

EXAMPLE 12

Low Strength Granule

| | |
|---|---|
| 2-[[(4-iodo-6-methoxypyrimidin-2-yl)aminocarbonyl]-aminosulfonyl]benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 13

Granule

| | |
|---|---|
| N'—[(4-iodo-6-methoxypyrimidin-2-yl)aminocarbonyl]-N,N—dimethyl-1,2-benzenedisulfonamide | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 14

High Strength Concentrate

| | |
|---|---|
| 2-[[(4-iodo-6-methoxypyrimidin-2-yl)aminocarbonyl]-aminosulfonyl]benzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 15

Wettable Powder

| | |
|---|---|
| 2-[[(4-iodo-6-methoxypyrimidin-2-yl)aminocarbonyl]-aminosulfonyl]benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 16

Wettable Powder

| | |
|---|---|
| 2-[[(4-iodo-6-methoxypyrimidin-2-yl)aminocarbonyl]-aminosulfonyl]benzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 17

Oil Suspension

| | |
|---|---|
| 2-[[(4-iodo-6-methoxypyrimidin-2-yl)aminocarbonyl]-aminosulfonyl]benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 18

Dust

| | |
|---|---|
| 2-[[(4-iodo-6-methoxypyrimidin-2-yl)aminocarbonyl]-aminosulfonyl]benzoic acid, methyl ester | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

Test results indicate that the compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice, wheat, barley, cotton, corn and soybeans. Alternatively, the subject compounds are useful to modify plant growth.

The rates of application for the compounds of the invention are determined by a number of factors, including their use as selective or general herbicides, the crop species involved, the type of weeds to be controlled, weather and climate, formulations selected, mode of application, amount of foliage present, etc. In general terms, the subject compounds should be applied at levels of around 0.01 to 5 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Compounds

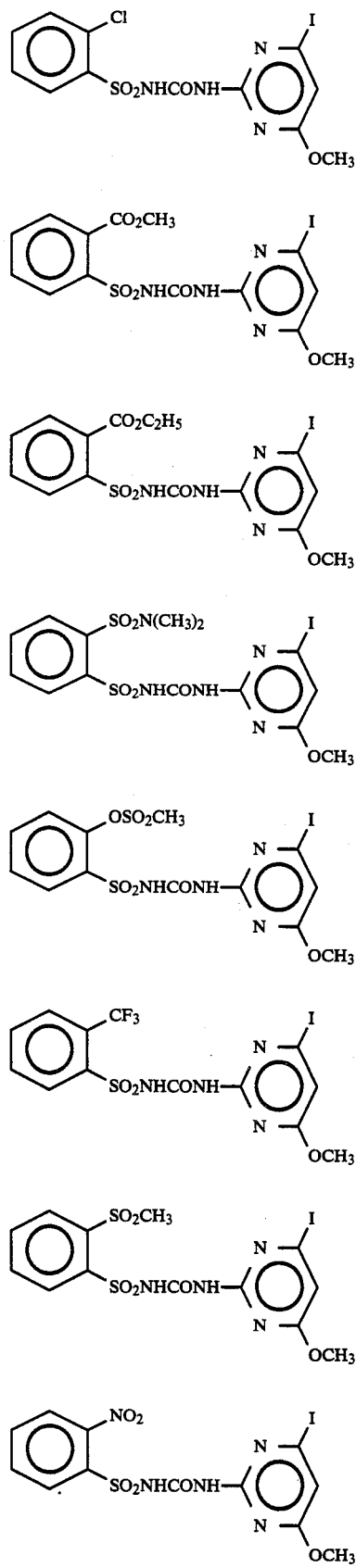

Compound 1
Compound 2
Compound 3
Compound 4
Compound 5
Compound 6
Compound 7
Compound 8

-continued
Compounds

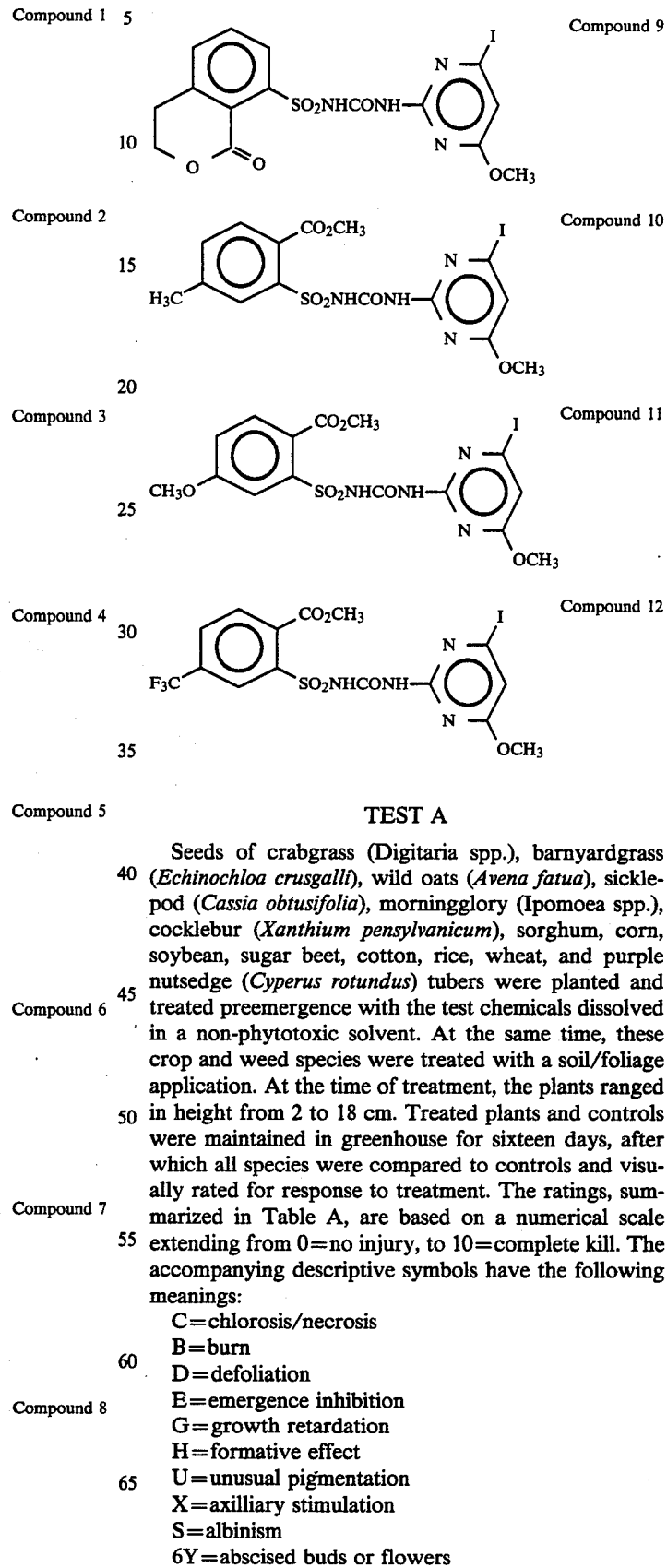

Compound 9
Compound 10
Compound 11
Compound 12

TEST A

Seeds of crabgrass (Digitaria spp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugar beet, cotton, rice, wheat, and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis
B=burn
D=defoliation
E=emergence inhibition
G=growth retardation
H=formative effect
U=unusual pigmentation
X=axilliary stimulation
S=albinism
6Y=abscised buds or flowers

TABLE A

| Rate (kg/ha) | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 | Cmpd. 9 0.05 | Cmpd. 10 0.05 | Cmpd. 11 0.05 | Cmpd. 12 0.05 |
|---|---|---|---|---|---|---|---|---|---|---|---|---|
| POSTEMERGENCE |||||||||||||
| Morningglory | 2C | 5C,9G | 1C,4G | 4C,9G | 5C,9G | 5C,9G | 3C,8H | 2C,8G | 9C | 5C,9G | 5C,9G | 2C |
| Cocklebur | 9C | 10C | 10C | 10C | 9C | 9C | 9C | 10C | 10C | 9C | 10C | 5C,9G |
| Cassia | 2C | 6C,9G | 2C,6G | 4C,8G | 5C,9G | 3C,5G | 3C,8H | 4C,9G | 9C | 9C | 4C,9G | 1C |
| Nutsedge | 2C | 3C,8G | 7G | 2C,5G | 2C,9G | 2C,9G | 2C,8G | 9C | 2C,9G | 5C,9G | 9C | 2C,5G |
| Crabgrass | 0 | 2C,6G | 2G | 4G | 4G | 3G | 2C,5G | 2C,4G | 5C,9G | 5C,8G | 3C,8G | 2G |
| Barnyardgrass | 0 | 3C,9H | 2C,9H | 3C,9H | 9H | 3C,8G | 3C,9H | 3C,8H | 9C | 5C,9H | 3C,7H | 2C,2G |
| Wild Oats | 0 | 2C,6G | 2G | 0 | 1C | 2C | 2G | 2G | 5C,9H | 1C | 3G | 0 |
| Wheat | 0 | 2C,4G | 2G | 1C,4G | 0 | 0 | 2G | 2G | 9C | 0 | 2G | 0 |
| Corn | 3G | 1U,7H | 2C,6H | 3H | 2C,9H | 3C,6G | 2C,8H | 2C,5G | 9C | 2C,8H | 9H | 0 |
| Soybean | 0 | 3C,5G | 3G | 1C,1H | 3C,7G | 3C,5G | 2C,2H | 3H | 2C,4H | 3C,8G | 4C,9G | 1H |
| Rice | 2G | 3C,8G | 2C,8G | 3C,8G | 2C,8G | 2C,8G | 4C,9G | 2C,7G | 5C,9G | 9G | 2C,8G | 0 |
| Sorghum | 0 | 2C,8G | 9G | 7H | 9G | 5G | 1C,9G | 5G | 5C,9G | 2C,9G | 3C,8H | 0 |
| Sugar Beets | 5C,9G | 4C,9G | 3C,8G | 3C,5G | 4C,8G | 4C,8G | 3C,7G | 9C | 10C | 9C | 5C,9G | 3C,7G |
| Cotton | 2C,4G | 9C | 5C,9G | 5C,9G | 9C | 6C,9G | 10C | 10C | 10C | 9C | 5C,9G | 3C,7G |
| PREEMERGENCE |||||||||||||
| Morningglory | 2C,8G | 9G | 5G | 7G | 9G | 9G | 9G | 9G | 9G | 9G | 9G | 6G |
| Cocklebur | 9H | 5G | 7H | 8G | 9H | — | 8H | — | 8G | — | 9G | 9H |
| Cassia | 6G | 5G | 0 | 5G | 7G | 8G | 8G | 7G | 8G | 7G | 8G | 6G |
| Nutsedge | 0 | 2G | 7G | 10E | 10E | 0 | 10E | 5G | 9G | 10E | 5G | 0 |
| Crabgrass | 0 | 0 | 0 | 0 | 5G | 2G | 7G | 0 | 3C,8G | 3G | 2G | 0 |
| Barnyardgrass | 1C | 3G | 4G | 5G | 4G | 3C,3H | 2C,8G | 0 | 2C,8G | 2C,7G | 3G | 0 |
| Wild Oats | 0 | 5G | 3G | 0 | 2C,4G | 2C,3G | 5G | 0 | 5G | 2C | 2C,6G | 0 |
| Wheat | 0 | 3G | 0 | 0 | 0 | 0 | 0 | 2G | 4G | 0 | 4G | 0 |
| Corn | 2C,6G | 6G | 4G | 5G | 2C,7G | 3C,6G | 8G | 1C,6G | 2C,8G | 3C,8G | 2C,8G | 2C,5G |
| Soybean | 0 | 0 | 0 | 0 | 2C,4H | 2C,3H | 3H | 2H | 2H | 0 | 3C,6G | 0 |
| Rice | 4G | 8G | 9G | 2C,7H | 7G | 3C,7G | 10E | 5G | 10E | 2C,7G | 6G | 0 |
| Sorghum | 3G | 7G | 5G | 6G | 8G | 2C,6G | 2C,9G | 3G | 2C,9G | 2C,9H | 8G | 0 |
| Sugar Beets | 9G | 7G | 8G | 6G | 9G | 9G | 8G | 8G | 4C,9G | 2C,8G | 9G | 3G |
| Cotton | 9G | 8G | 4G | 10E | 9G | 8G | 9G | 9G | 9G | 9G | 9G | 7G |

TEST B

Postemergence

Two round pans (25 cm diameter by 12.5 cm deep) were filled with sassafras sandy loam soil. One pan was planted with blackgrass (*Alopecurus myosuroides*), sugar beets, nutsedge (*Cyperus rotundus*) tubers, crabgrass, (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faverii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with sassafras sandy loam soil. One pan was planted with blackgrass, sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response. The response rating system was described for Test A.

Response ratings are contained in Table B.

TABLE B

| | Compound 2 | | | Compound 4 | | | | Compound 5 | | | Compound 6 | | | Compound 7 | | | Compound 10 | | Compound 11 | | | |
|---|---|---|---|---|---|---|---|---|---|---|---|---|---|---|---|---|---|---|---|---|---|---|
| Rate (g/ha) | 62 | 16 | 04 | 250 | 62 | 16 | 04 | 62 | 16 | 04 | 250 | 62 | 16 | 250 | 62 | 16 | 62 | 04 | 62 | 16 | 04 | 01 |
| POSTEMERGENCE ||||||||||||||||||||||||
| Corn | 5G | 0 | 0 | 3G | 2G | 0 | 0 | 4G | 0 | 0 | 0 | 0 | 0 | 8G | 3G | 0 | 2G | 0 | 7G | 3G | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 9G | 5G | 2G | 9G | 8G | 5G | 0 | 5G | 0 | 0 | 7G | 3G | 0 | 9G | 5G | 2G | 5G | 0 | 2G | 0 | 0 | 0 |
| Soybean | 2G | 0 | 0 | 2G | 0 | 0 | 0 | 0 | 0 | 0 | 2G | 0 | 0 | 4G | 2G | 0 | 0 | 0 | 8G | 3G | 0 | 0 |
| Cotton | 9G | 7G | 2G | 9G | 8G | 6G | 2G | 7G | 4G | 0 | 6G | 2G | 0 | 9G | 7G | 3G | 7G | 0 | 10C | 10C | 8G | 0 |
| Sugar beet | 9G | 8G | 2G | 9G | 7G | 3G | 0 | 7G | 2G | 0 | 9G | 7G | 3G | 7G | 0 | 0 | 9G | 6G | 10C | 9G | 5G | 2G |
| Crabgrass | 7G | 3G | 0 | 9G | 9G | 8G | 4G | 6G | 2G | 0 | 6G | 2G | 0 | 9G | 3G | 0 | 6G | 2G | 3G | 0 | 0 | 0 |
| Johnsongrass | 8G | 7G | 3G | 9G | 7G | 5G | 0 | 8G | 3G | 0 | 5G | 2G | 0 | 10G | 9G | 9G | 10G | 5G | 6G | 2G | 0 | 0 |
| Blackgrass | 8G | 7G | 2G | 10G | 9G | 5G | 0 | 2G | 0 | 0 | 4G | 0 | 0 | 8G | 4G | 0 | 4G | 0 | 2G | 0 | 0 | 0 |
| Barnyardgrass | 9G | 8G | 4G | 9G | 8G | 4G | 0 | 7G | 3G | 0 | 7G | 2G | 0 | 9G | 8G | 7G | 8G | 2G | 5G | 0 | 0 | 0 |
| Nutsedge | 9G | 4G | 0 | 9G | 8G | 5G | 2G | 9G | 4G | 0 | 6G | 0 | 0 | 9G | 8G | 3G | 9G | 4G | 5G | 2G | 0 | 0 |
| Giant Foxtail | 6G | 2G | 0 | 8G | 6G | 2G | 0 | 9G | 2G | 0 | 4G | 0 | 0 | 9G | 9G | 6G | 8G | 0 | 3G | 0 | 0 | 0 |
| Wild Oats | 4G | 0 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | 9G | 7G | 0 | 10G | 9G | 4G | 0 | 9G | 5G | 0 | 9G | 6G | 0 | 9G | 9G | 3G | 10G | 5G | 10C | 8G | 6G | 2G |
| Morningglory | 9G | 8G | 2G | 10G | 7G | 3G | 0 | 9G | 4G | 0 | 9G | 2G | 0 | 10G | 9G | 2G | 8G | 0 | 10G | 10G | 4G | 0 |
| Teaweed | 9G | 5G | 0 | 9G | 9G | 8G | 2G | 9G | 7G | 2G | 9G | 7G | 2G | 10G | 6G | 2G | 9G | 4G | 8G | 7G | 4G | 2G |
| Cassia | 9G | 5G | 0 | 9G | 9G | 6G | 2G | 10G | 9G | 3G | 9G | 8G | 3G | 9G | 5G | 3G | 10C | 5G | 10C | 9G | 7G | 5G |
| Jimsonweed | 9G | 7G | 3G | 10G | 8G | 6G | 2G | 10G | 5G | 0 | 9G | 9G | 2G | 10G | 8G | 6G | 9G | 3G | 10C | 9G | 8G | 3G |

TABLE B-continued

| Velvetleaf | 9G | 7G | 4G | 9G | 9G | 7G | | 3G | 9G | 4G | 0 | 9G | 8G | 3G | 10G | 9G | 3G | 9G | 6G | 10C | 7G | 5G | 0 |
|---|---|---|---|---|---|---|---|---|---|---|---|---|---|---|---|---|---|---|---|---|---|---|---|
| Rate (g/ha) | 250 | 62 | 16 | 250 | 62 | | 250 | 62 | 16 | 250 | 62 | | 250 | 62 | 16 | 250 | 62 | | 250 | 62 | 250 | 62 | 16 |
| PREEMERGENCE |||||||||||||||||||||||
| Corn | 3G | 0 | 0 | 0 | 0 | | 5G | 2G | 0 | 0 | 0 | | 7G | 5G | 0 | 2G | 0 | | 3G | 0 | 0 | | |
| Wheat | 3G | 0 | 0 | 0 | 0 | | 0 | 0 | 0 | 0 | 0 | | 0 | 0 | 0 | 0 | 0 | | 0 | 0 | 0 | | |
| Rice | 9G | 9G | 8G | 9G | 8G | | 9G | 6G | 4G | 9G | 7G | | 9G | 9G | 8G | 9G | 8G | | 8G | 8G | 4G | 0 | |
| Soybean | 3G | 0 | 0 | 0 | 0 | | 0 | 0 | 0 | 0 | 0 | | 0 | 0 | 0 | 4G | 0 | | 3G | 0 | 0 | | |
| Cotton | 6G | 3G | 0 | 2G | 0 | | 5G | 2G | 0 | 2G | 0 | | 3G | 0 | 0 | 5G | 0 | | 6G | 2G | 0 | | |
| Sugar beet | 8G | 7G | 3G | 5G | 3G | | 6G | 3G | 0 | 7G | 3G | | 3G | 0 | 0 | 7G | 3G | | 10G | 10G | 6G | | |
| Crabgrass | 8G | 7G | 2G | 9G | 3G | | 7G | 3G | 0 | 0 | 0 | | 9G | 4G | 2G | 9G | 5G | | 5G | 2G | 0 | | |
| Johnsongrass | 9G | 8G | 3G | 8G | 6G | | 8G | 6G | 2G | 3G | 0 | | 9G | 9G | 4G | 10G | 9G | | 5G | 0 | 0 | | |
| Blackgrass | 9G | 9G | 8G | 9G | 9G | | 8G | 6G | 2G | 8G | 6G | | 9G | 9G | 6G | 8G | 7G | | 8G | 6G | 0 | 2G | |
| Barnyardgrass | 9G | 7G | 3G | 9G | 7G | | 8G | 4G | 0 | 6G | 2G | | 9G | 8G | 4G | 9G | 7G | | 4G | 0 | 0 | | |
| Nutsedge | 9G | 8G | 0 | 9G | 8G | | 9G | 9G | 3G | 2G | 0 | | 10E | 9G | 3G | 9G | 8G | | 8G | 3G | 0 | | |
| Giant Foxtail | 10E | 7G | 2G | 9G | 8G | | 8G | 3G | 0 | 8G | 2G | | 8G | 7G | 3G | 9G | 7G | | 5G | 0 | 0 | | |
| Wild Oats | 6G | 4G | 0 | 0 | 0 | | 0 | 0 | 0 | 0 | 0 | | 0 | 0 | 0 | 2G | 0 | | 0 | 0 | 0 | | |
| Cocklebur | 7G | 3G | 0 | 6G | 0 | | 6G | 3G | 0 | 6G | 0 | | 0 | 0 | 0 | 9G | 6G | | 4G | 2G | 0 | | |
| Morningglory | 8G | 4G | 0 | 7G | 0 | | 7G | 3G | 0 | 3G | 0 | | 3G | 0 | 0 | 8G | 5G | | 5G | 2G | 0 | | |
| Teaweed | 9G | 9G | 4G | 9G | 7G | | 8G | 5G | 0 | 8G | 3G | | 9G | 6G | 0 | 9G | 8G | | 10G | 8G | 5G | | |
| Cassia | 8G | 6G | 2G | 7G | 2G | | 7G | 2G | 0 | 4G | 0 | | 4G | 0 | 0 | 7G | 0 | | 10G | 9G | 4G | | |
| Jimsonweed | 9G | 7G | 4G | 9G | 9G | | 9G | 8G | 3G | 9G | 7G | | 9G | 8G | 7G | 9G | 7G | | 10G | 9G | 3G | | |
| Velvetleaf | 9G | 8G | 4G | 7G | 5G | | 8G | 4G | 0 | 8G | 6G | | 7G | 0 | 0 | 9G | 7G | | 10G | 9G | 3G | | |

What is claimed is:

1. A compound of the formula

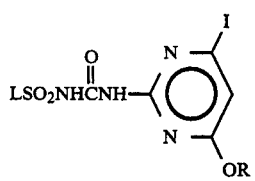

wherein
R is CH$_3$ or CH$_2$CH$_3$;

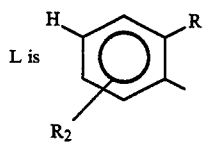 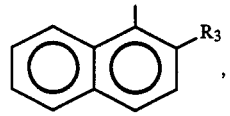

L-1, L-2

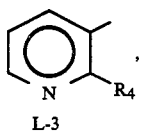 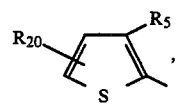

L-3, L-4

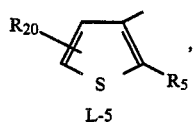 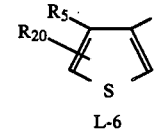

L-5, L-6

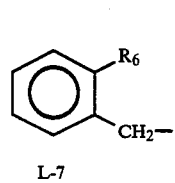 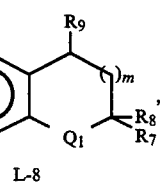

L-7, L-8

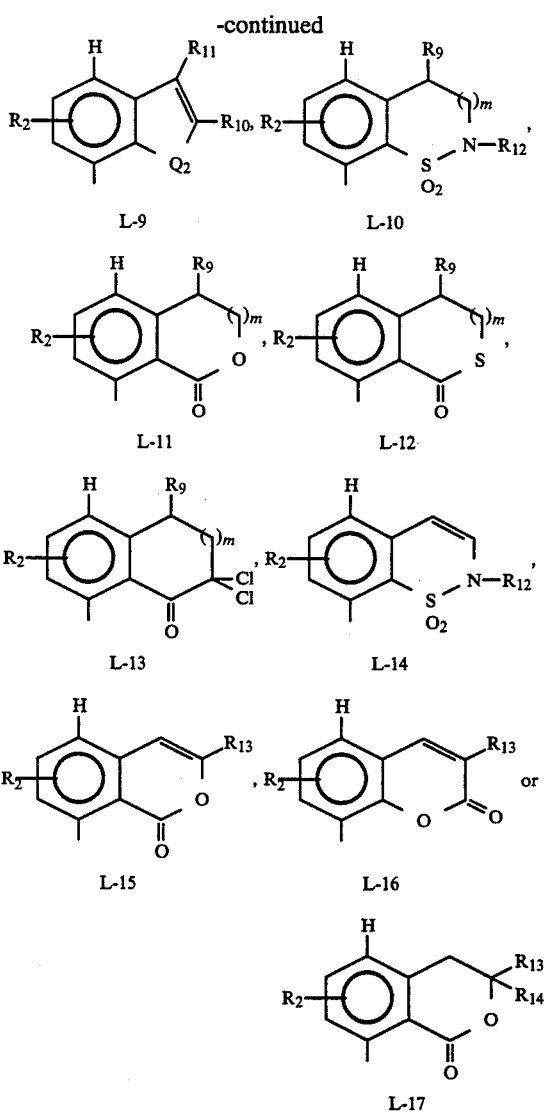

L-9, L-10, L-11, L-12, L-13, L-14, L-15, L-16, L-17

R$_1$ is C$_1$-C$_4$ alkyl, C$_1$-C$_4$ alkoxy, OCH$_2$CH$_{2l}$ $_{OCH_3}$, F, Cl, Br, NO$_2$, CF$_3$, CO$_2$R$_{15}$, SO$_2$NR$_{16}$R$_{17}$, C(O)R$_{21}$, CR$_{21}$(OR$_{22}$)$_2$, SO$_2$N(OCH$_3$)CH$_3$, OSO$_2$R$_{18}$, $S(O)_nR_{19}$, $WCF_3$, $WCHF_2$, $C_3-C_4$ alkenyloxy, $C_3-C_4$ alkynyloxy, $C_1-C_2$ alkyl substituted with $OCH_3$ or $OCH_2CH_3$, $C_6H_5$,

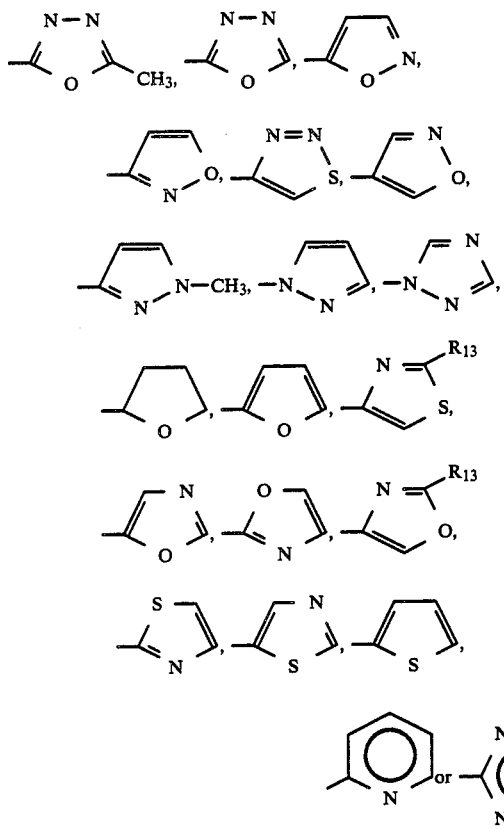

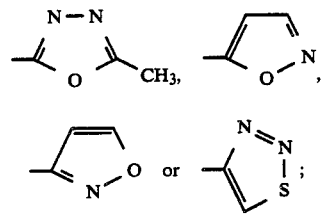

$R_2$ is H, F, Cl, Br, $C_1-C_4$ alkyl, $C_1-C_4$ alkoxy, $C_3-C_4$ alkenyloxy, $C_3-C_4$ alkynyloxy, $C_1-C_4$ haloalkoxy, $C_1-C_4$ haloalkyl, $S(O)_pC_1-C_4$ alkyl, $S(O)_pC_3-C_4$ alkenyl, $S(O)_pC_3-C_4$ alkynyl or $C_1-C_2$ alkyl substituted with $OCH_3$ or $SCH_3$;

$R_3$ is H, $CH_3$, $OCH_3$, F, Cl, Br, $SO_2N(CH_3)_2$, $OSO_2CH_3$ or $S(O)_nCH_3$;

$R_4$ is $CH_3$, $CH_2CH_3$, $OCH_3$, $OCH_2CH_3$, F, Cl, Br, $SO_2NR_{16}R_{17}$, $SO_2N(OCH_3)CH_3$, $S(O)_nR_{19}$, $C_3-C_4$ alkenyloxy or $C_3-C_4$ alkynyloxy;

$R_5$ is $C_1-C_3$ alkyl, F, Cl, Br, $NO_2$, $CO_2R_{15}$, $SO_2NR_{16}R_{17}$, $SO_2N(OCH_3)CH_3$ or $S(O)_nR_{19}$;

$R_6$ is Cl, $NO_2$, $CO_2CH_3$, $CO_2CH_2CH_3$, $SO_2N(CH_3)_2$, $OSO_2CH_3$, $SO_2CH_3$, $SO_2CHCH_3$, $OCH_3$ or $OCH_2CH_3$;

$R_7$ is H, $CH_3$ or $CH_2CH_3$;
$R_8$ is H, $CH_3$ or $CH_2CH_3$;
$R_9$ is H or $CH_3$;
$R_{10}$ is H or $CH_3$;
$R_{11}$ is H or $CH_3$;
$R_{12}$ is H, $C_1-C_4$ alkyl, $C_3-C_4$ alkenyl, $C_3-C_4$ alkynyl, benzyl, $C_1-C_4$ alkylcarbonyl, $C_1-C_4$ alkoxycarbonyl, $CH_2CN$, $CH_2C(O)CH_3$, $CH_2CO_2(C_1-C_2$ alkyl), $C_1-C_4$ alkyl sustituted with 0-3F, 0-1Cl, OH, $OCH_3$ or $OC_2H_5$ or $C_3-C_4$ alkenyl substituted with 1-3F or 1-3Cl;

$R_{13}$ is H or $CH_3$;
$R_{14}$ is $CH_3$ or $C_2H_5$;
$R_{15}$ is $C_1-C_4$ alkyl, $CH_2CH_2OCH_3$, $CH_2CH_2Cl$ or $CH_2CH=CH_2$;
$R_{16}$ is H, $C_1-C_3$ alkyl;
$R_{17}$ is $C_1-C_3$ alkyl;
$R_{18}$ is $C_1-C_3$ alkyl or $N(CH_3)_2$;
$R_{19}$ is $C_1-C_3$ alkyl or $CH_2CH=CH_2$;
$R_{20}$ is H, Cl or $CH_3$;
$R_{21}$ is H, $C_1-C_4$ alkyl, $C_3-C_4$ alkenyl, $C_3-C_4$ alkynyl or $C_3-C_6$ cycloalkyl;
$R_{22}$ is $C_1-C_2$ alkyl;
m is 0 or 1;
n is 0 or 2;
p is 0, 1 or 2;
$Q_1$ is O, S or $SO_2$;
$Q_2$ is O or S; and
W is O, S or $SO_2$;
provided that
(1) the total number of carbon atoms of $R_{16}$ and $R_{17}$ is less than or equal to four; and
(2) when m is 1, then $R_9$ is H;
and their agriculturally suitable salts.

2. Compounds of claim 1 where R is $CH_3$.
3. Compounds of claim 2 where L is L-1, L-2, L-3, L-5, L-8, L-10, L-11, L-16 or L-17.
4. Compounds of claim 3 wherein
L is L-1;
$R_1$ is $OCH_3$, $OC_2H_5$, Cl, $NO_2$, $CF_3$, $CO_2CH_3$, $CO_2C_2H_5$, $SO_2N(CH_3)_2$, $SO_2N(OCH_3)CH_3$, $OSO_2R_{18}$, $S(O)_nR_{19}$, $OCF_2H$, $SCF_2H$, $C(O)CH_3$, $C(O)C_2H_5$, $OCH_2CH=CH_2$, $OCH_2C\equiv CH$,

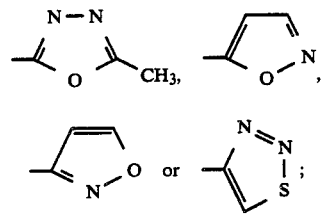

$R_2$ is H, F, Cl, Br, $CH_3$, $C_2H_5$, $S(O)_pC_1-C_2$ alkyl, $S(O)_pCH_2CH=CH_2$, $S(O)_pCH_2C\equiv CH$, $C_1-C_3$ alkoxy, $OCH_2CH=CH_2$, $OCH_2C\equiv CH$, $C_1-C_2$ haloalkoxy, $C_1-C_2$ haloalkyl, $CH_2OH_3$ or $CH_2SCH_3$;
$R_{18}$ is $C_1-C_3$ alkyl;
$R_{19}$ is $CH_3$ or $C_2H_5$; and
n is 2.

5. Compounds of claim 4 where
L is

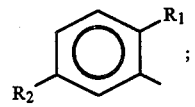

and
$R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.

6. Compounds of claim 3 where
L is L-2; and
$R_3$ is Cl, $CH_3$, $OCH_3$, $SCH_3$ or Br.

7. Compounds of claim 3 where
L is L-3; and
$R_4$ is Cl, $SO_2CH_3$ or $SO_2N(CH_3)_2$.

8. Compounds of claim 3 where
$R_{20}$ is H;
L is L-5; and
$R_5$ is $CO_2CH_3$ or $CO_2C_2H_5$.

9. Compounds of claim 3 where L is L-8.

10. Compounds of claim 3 where
   $R_9$ is H;
   $R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$,
   L is L-10; and
   $R_{12}$ is H, $C_1$–$C_4$ alkyl, $C_1$–$C_4$ alkylcarbonyl, $CH_2F$ or $C_2$–$C_3$ alkyl substituted with 1F or 1Cl.

11. Compounds of claim 3 where
   L is L-11;
   $R_9$ is H; and
   $R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.

12. Compounds of claim 3 where
   L is L-16;
   $R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.

13. Compounds of claim 3 where
   L is L-17;
   $R_2$ is H, F, Cl, Br, $CH_3$, $CH_2CH_3$, $SCH_3$, $SC_2H_5$, $OCH_3$, $OC_2H_5$, $CF_3$, $CH_2OCH_3$ or $CH_2SCH_3$.

14. The compound of claim 1 which is 2-[[(4-iodo-6-methoxypyrimidin-2-yl)aminocarbonyl]aminosulfonyl]-benzoic acid, methyl ester.

15. The compound of claim 1 which is N'-[(4-iodo-6-methoxypyrimidin-2-yl)aminocarbonyl]-N,N-dimethyl-1,2-benzenedisulfonamide.

16. The compound of claim 1 which is 2-[[(4-iodo-6-methoxypyrimidin-2-yl)aminocarbonyl]aminosulfonyl]-4-methylbenzoic acid, methyl ester.

17. A composition suitable for controlling the growth of undesired vegetation which comprises an effective amount of a compound of claim 1 and at least one of the following: surfactant, solid or liquid diluent.

18. A composition suitable for controlling the growth of undesired vegetation which comprises an effective amount of a compound of claim 2 and at least one of the following: surfactant, solid or liquid diluent.

19. A composition suitable for controlling the growth of undesired vegetation which comprises an effective amount of a compound of claim 3 and at least one of the following: surfactant, solid or liquid diluent.

20. A composition suitable for controlling the growth of undesired vegetation which comprises an effective amount of a compound of claim 4 and at least one of the following: surfactant, solid or liquid diluent.

21. A composition suitable for controlling the growth of undesired vegetation which comprises an effective amount of a compound of claim 5 and at least one of the following: surfactant, solid or liquid diluent.

22. A composition suitable for controlling the growth of undesired vegetation which comprises an effective amount of a compound of claim 6 and at least one of the following: surfactant, solid or liquid diluent.

23. A composition suitable for controlling the growth of undesired vegetation which comprises an effective amount of the compound of claim 7 and at least one of the following: surfactant, solid or liquid diluent.

24. A composition suitable for controlling the growth of undesired vegetation which comprises an effective amount of the compound of claim 8 and at least one of the following: surfactant, solid or liquid diluent.

25. A method for controlling the growth of undesired vegetation which comprises applying to the locus to be protected an effective amount of a compound of claim 1.

26. A method for controlling the growth of undesired vegetation which comprises applying to the locus to be protected an effective amount of a compound of claim 2.

27. A method for controlling the growth of undesired vegetation which comprises applying to the locus to be protected an effective amount of a compound of claim 3.

28. A method for controlling the growth of undesired vegetation which comprises applying to the locus to be protected an effective amount of a compound of claim 4.

29. A method for controlling the growth of undesired vegetation which comprises applying to the locus to be protected an effective amount of a compound of claim 5.

30. A method for controlling the growth of undesired vegetation which comprises applying to the locus to be protected an effective amount of a compound of claim 6.

31. A method for controlling the growth of undesired vegetation which comprises applying to the locus to be protected an effective amount of the compound of claim 7.

32. A method for controlling the growth of undesired vegetation which comprises applying to the locus to be protected an effective amount of the compound of claim 8.

* * * * *